US006319683B1

(12) United States Patent
James et al.

(10) Patent No.: US 6,319,683 B1
(45) Date of Patent: Nov. 20, 2001

(54) METHOD AND COMPOSITION FOR CONTROLLING FORMALDEHYDE FIXATION BY DELAYED QUENCHING

(75) Inventors: William M. James, Darnestown; Stephen W. Hoag, Cantonsville, both of MD (US)

(73) Assignee: Intergen Company, Purchase, NY (US)

( * ) Notice: Subject to any disclaimer, the term of this patent is extended or adjusted under 35 U.S.C. 154(b) by 0 days.

(21) Appl. No.: 08/824,708

(22) Filed: Apr. 14, 1997

Related U.S. Application Data

(63) Continuation-in-part of application No. 08/631,440, filed on Apr. 12, 1996, now abandoned.

(51) Int. Cl.$^7$ .................................................. C07C 45/00
(52) U.S. Cl. ........................... 435/40.5; 435/1.1; 435/1.2; 435/3; 435/40.52; 568/420; 568/422; 568/449; 514/694; 424/466; 424/474; 424/477
(58) Field of Search .............................. 435/1.1, 1.2, 1.3, 435/3, 40.5, 40.52; 424/466, 474, 477; 514/694; 568/420, 422, 449; 427/4; 71/64.11, 28; 252/186.25; 510/349; 523/207, 210, 211; 525/936; 210/728, 729, 749

(56) References Cited

U.S. PATENT DOCUMENTS

| 2,544,944 | 5/1951 | Ferrari, Jr. ............................ 379/197 |
| 3,197,302 | 7/1965 | MacBride et al. ........................ 71/37 |
| 3,862,300 | 1/1975 | Wertlake et al. .................. 435/40.52 |
| 3,896,033 | * 7/1975 | Grimm, III .............................. 400/113 |
| 3,912,490 | * 10/1975 | Boghosian .............................. 71/28 |
| 4,687,489 | 8/1987 | Rieke et al. .............................. 8/506 |
| 4,871,549 | 10/1989 | Ueda et al. ............................ 424/494 |
| 5,108,621 | 4/1992 | Robins ................................ 210/728 |
| 5,186,732 | * 2/1993 | Thompson et al. .................. 71/64.11 |
| 5,244,787 | 9/1993 | Key et al. .............................. 435/7.9 |
| 5,260,048 | 11/1993 | Ryan .................................... 435/40.5 |
| 5,478,722 | 12/1995 | Caldwell ................................ 435/1.1 |
| 5,597,977 | * 1/1997 | Chattopadhyay ........................ 149/6 |
| 5,609,871 | * 3/1997 | Michael et al. .................... 424/184.1 |
| 5,637,319 | 6/1997 | Takada ................................ 424/463 |
| 5,648,222 | 7/1997 | Tse et al. .............................. 435/7.23 |

FOREIGN PATENT DOCUMENTS

| 0210540 B1 | 10/1991 | (EP) . |
| 1010773 | 11/1965 | (GB) . |
| 08337521 | 6/1995 | (JP) . |
| WO94/07532 | 4/1994 | (WO) . |

OTHER PUBLICATIONS

"Remington: The Science and Practice of Pharmacy", vol. II, (1995) (Mack Publishing: Easton, PA) p. 1615–1649.*
Ishino, et al., "Design and preparation of pulsatile release tablet as a new oral drug delivery system", *Chem. Pharm. Bull.* (Tokyo), vol. 40, No. 11 (Nov. 1992), p. 3036. (Abstract only).

Narisawa, et al., "An organic acid–induced sigmoidal release system for oral controlled–release preparations", *Pharm. Res.*, vol. 11, No. 1 (Jan. 1994), p. 111 (Abstract only).
Yoshino, "Design and evaluation of time–controlled oral drug delivery system", *Membrane*, vol. 19, No. 6 (1994), p. 392. (Abstract only).
Narisawa, et al., "Drug release behavior in gastrointestinal tract of beagle dogs from multiple unit type rate–controlled or time–controlled release preparations coated with insoluble polymer–based film", *Journal of Controlled Release*, vol. 33, No. 2 (1995), p. 253. (Abstract only).
Narisawa, et al., "An organic acid–induced sigmoidal release system for oral controlled–release preparations. 2. Permeability enhancement of Eudragit RS coating led by the physicochemical interactions with organic acid", *J. Pharm. Sci.*, vol. 85, No. 2 (Feb. 1996), p. 184. (Abstract only).
Narisawa, et al., "An organic acid–induced sigmoidal release system for oral controlled–release system for oral–-controlled–release preparations: III. Elucidations of the anomalous drug release behavior through osmotic pumping mechanism", *International Journal of Pharmaceutics* (Amsterdam), vol. 148, No. 1 (1977), p. 85. (Abstract only).
Ueda, et al., "Development of a novel drug release system, time–controlled explosion system (TES)", *Journal of Drug Targeting*, vol. 2, No. 1 (1994), p. 35. (Abstract only).
Ueda, et al., "Development of a novel drug release system, time controlled explosion system (TES): II: Design of multiparticulate TES and in vitro drug release properties", *Chemical & Pharmaceutical Bulletin* (Tokyo), vol. 42, No. 2 (1994), p. 359. (Abstract only).
Ueda, et al., "Development of a novel drug release system, time–controlled explosion system (TES): III: Relation between lag time and membrane thickness", *Chemical & Pharmaceutical Bulletin* (Tokyo), vol. 42, No. 2 (1994), p. 364. (Abstract only).
Ueda, et al., "Development of a novel drug delivery system, time–controlled explosion system (TES). IV. In vivo drug release behavior", *J. Drug Target*, vol. 2, No. 2 (1994), p. 133. (Abstract only).
Kimura, et al., "Development of time–controlled explosion system (TES)", *Membrane*, vol. 20, No. 4 (1995), p. 263. (Abstract only).
Takaya, et al., "Importance of dissolution process on systemic availability of drugs delivered by colon delivery system", *Journal of Controlled Release*, vol. 50, Nos. 1–3 (1998), p. 111. (Abstract only).

(List continued on next page.)

*Primary Examiner*—Leon B. Lankford, Jr.
(74) *Attorney, Agent, or Firm*—Foley & Lardner

(57) ABSTRACT

A method and composition for quenching formaldehyde fixation of cell and tissue specimens. The composition includes a formaldehyde-reactive agent. The formaldehyde-reactive agent reacts with the formaldehyde to quench the fixation of the cell or tissue specimen. The method involves contacting a formaldehyde fixative solution with the composition.

84 Claims, 8 Drawing Sheets

OTHER PUBLICATIONS

Bankfalvi, et al., "Wet Autoclave Pretreatment For Antigen Retrieval in Diagnostic Immunohistochemistry", *Journal of Pathology* (1994), vol. 174, p. 223. (First page only).

Battifora, "Assessment of antigen damage in immunohistochemistry. The vimentin internal control", *Am. J. Clin. Pathol.*, vol. 96, No. 5 (1991), p. 669. (Abstract only).

Battifora, et al., "The Influence of Protease Digestion and Duration of Fixation on the Immunostaining of Keratins", *The Journal of Histochemistry and Cytochemistry*, vol. 34, No. 8 (1986), pp. 1095–1100.

Cattoretti, et al., "Antigen Unmasking On Formalin–Fixed, Paraffin–Embedded Tissue Sections", *Journal of Pathology*, vol. 171 (1993), pp. 83–98.

Clark, et al., *Staining Procedures*, Williams & Wilkins (Baltimore/London), 4th Ed. (1981), pp. 11–23.

Elias, et al., "Quality control in immunohistochemistry. Report of a workshop sponsored by the Biological Stain Commission", *Am. J. Clin. Pathol.*, vol. 92, No. 6 (1989), p. 836. (Abstract only).

Feldman, "Reactions of Nucleic Acids and Nucleoproteins with Formaldehyde", *Progress in Nucleic Acid Research and Molecular Biology*, Academic Press (New York/London), vol. 13 (1973), pp. 1–49.

Fox, et al., "Formaldehyde Fixation", *The Journal of Histochemistry and Cytochemistry*, vol. 33, No. 8 (1985), pp. 845–853.

Greer, et al., "Sample Preparation and PCR Amplification from Paraffin–embedded Tissues", *Cold Spring Habor ISSN*, vol. 3 (1992), pp. S113–S115.

Huang, et al., "Application of immunofluorescent staining on paraffin sections improved by trypsin digestion", *Lab Invest.*, vol. 35, No. 4 (Oct. 1976), p. 383. (Abstract only).

Karlsen, et al., "Modifications of human and viral deoxyribonucleic acid by formaldehyde fixation", *Lab Invest.*, vol. 71, No .4 (Oct. 1994), p.604. (Abstract only).

Leong, et al., "The Effects of Progressive Formaldehyde Fixation on The Preservation of Tissue", *Pathology*, vol. 21 (1989), pp. 266–268.

Mason, et al., "Effects of formaldehyde fixation on protein secondary structure: a calorimetric and infrared spectroscopic investigation", *J. Histochem. Cytochem.*, vol. 39, No. 2, (Feb. 1991), p. 225. (Abstact only).

O'Leary, et al., "The importance of fixation procedures on DNA template and its suitability for solution–phase polymerase chain reaction and PCR in situ hybridization", *Histochem J.*, vol. 26, No. 4 (Apr. 1994), p. 337. (Abstract only).

Overton, et al., "Method to Make Paraffin–Embedded Breast and Lymph Tissue Mimic Fresh Tissue in DNA Analysis", *Cytometry*, vol. 26 (1996), p. 166. (First page only).

Overton, et al., "Reversing the effect of formalin on the binding of propidium iodide to DNA", *Cytometry*, vol. 16, No. 4 (Aug. 1, 1994), p. 351. (Abstract only).

Shi, et al., "Anitgen Retrieval in Formalin–fixed, Paraffin–embedded Tissues: An Enhancement Method for Immunohistochemical Staining Based on Microwave Oven Heating of Tissue Sections", *The Journal of Histochemistry and Cytochemistry*, vol. 39, No. 6 (1991), pp. 741–748.

Shi, et al., "Antigen Retrieval Immunohistochemistry: Past, Present, and Future", *The Journal of Histochemistry & Cytochemistry*, vol. 45, No. 3 (1997), pp. 327–343.

Silvestrini, et al., "Immunohistochemical Detection of p53 in Clinical Breast Cancers: a Look at Methodologic Approaches", *Journal of the National Cancer Institute*, vol. 87, No. 13 (Jul. 5, 1995), p. 20.

O'Leary, et al., "The importance of fixation procedures on DNA template and its suitability for solution–phase polymerase chain rection and PCR in situ hybridization", *Histochem J.*, vol. 26, No. 4 (1994), p. 337 (Abstact only).

Walker, "Paraformaldehyde", *Formaldehyde*, Reinhold Publishing (New York) (1944), pp. 69, 70, 73.

Walker, "Chemical Properties of Formaldehyde", *Formaldehyde*, Reinhold Publishing (New York) (1944), pp. 102–116.

Walker, "Reactions of Formaldehyde with Inorganic Agents", *Formaldehyde*, Reinhold Publishing (New York) (1944), pp. 117–137.

Walker, "Reactions with Amino and Amino Compounds", *Formaldehyde*, Reinhold Publishing (New York) (1944), pp. 208–226.

Walker, "Hexamethylenetetramine", *Formaldehyde*, Reinhold Publishing (New York) (1944), pp. 276–296.

Baker, *Controlled Release of Biologically Active Agent*, John Wiley & Sons, Inc. (Canada) (1987), pp. 1–7.

Harris, et al., "Aqueous Polymeric Coating for Modified Release Oral Dosage Forms", *Aqueous Polymeric Coating for Pharmaceuticals Dosages Forms*, Marcel Dekker, Inc. (New York) (1997), pp. 81–91, 128–133.

\* cited by examiner

FIG. IA
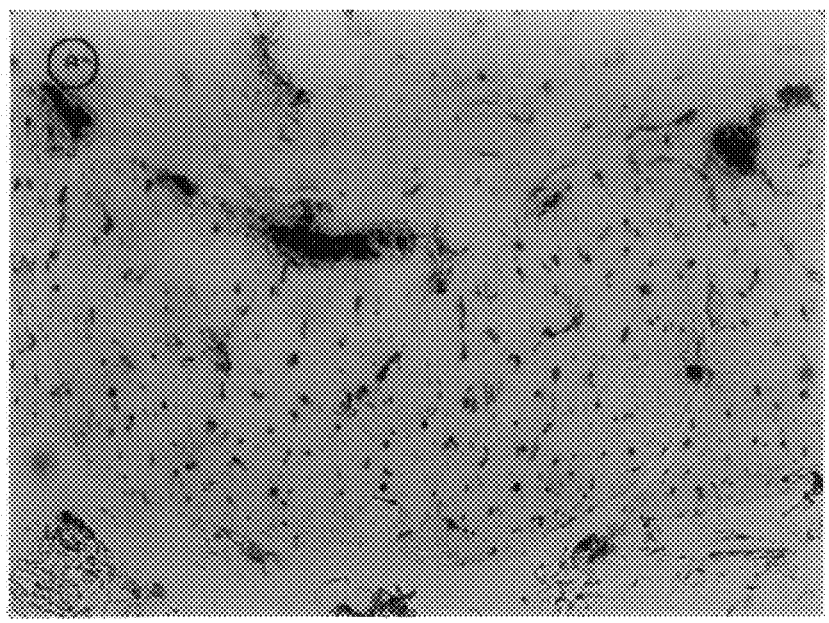
FIG. IB
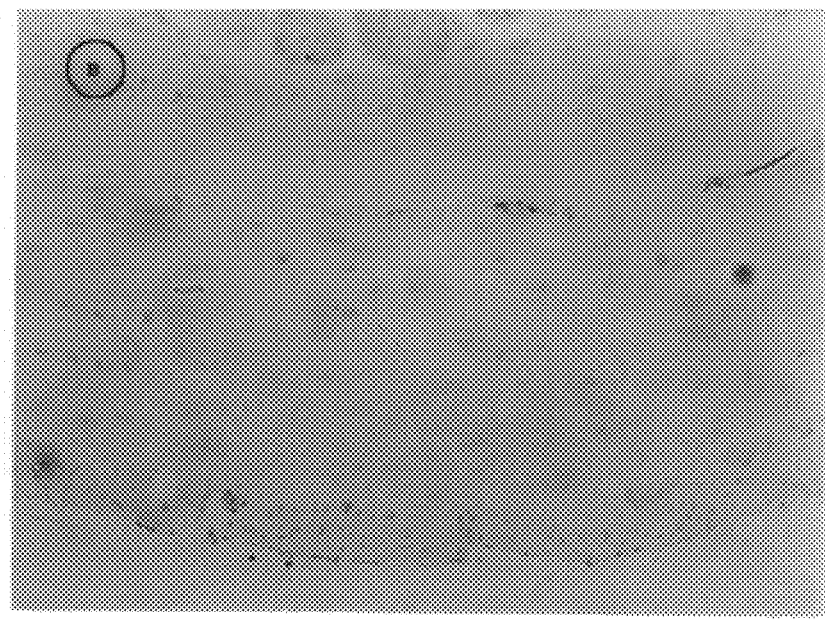

FIG. IC
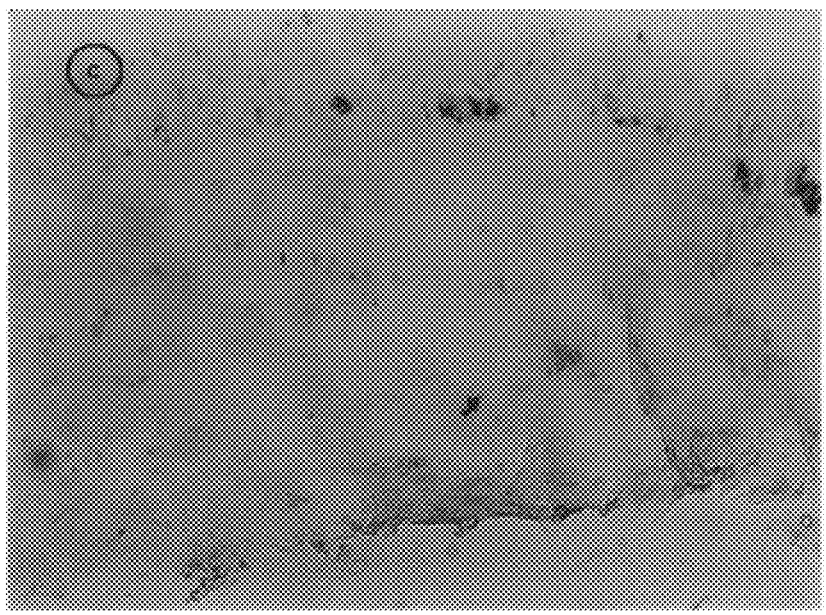
FIG. ID
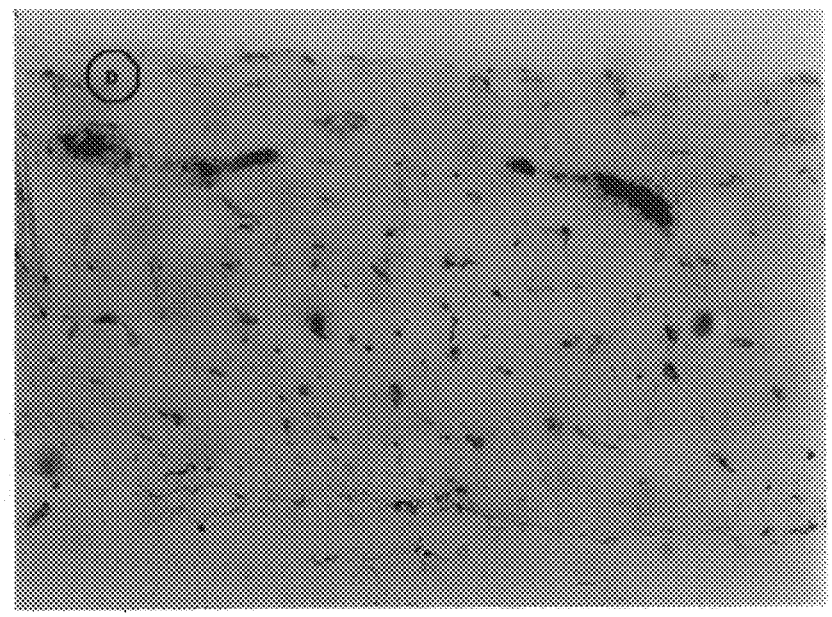

CALIBRATION OF FORMALDEHYDE ASSAY (ACATYLACATONE REACTION)

REACTION OF FORMALDEHYDE (NBF) WITH UREA AT THREE MOLE RATIOS (UREA:FORMALDEHYDE)

REACTION OF AMMONIUM ACETATE WITH FORMALDEHYDE, AT A RATIO OF 1.5 MOLES NH4 PER 1.0 MOLE FORMALDEHYDE

METHOD AND COMPOSITION FOR CONTROLLING FORMALDEHYDE FIXATION BY DELAYED QUENCHING

RELATED APPLICATION

This is a continuation-in-part of copending U.S. application Ser. No. 8/631,440 filed Apr. 12, 1996 abandoned.

FIELD OF THE INVENTION

The present invention generally relates to the fixation of cell and tissue specimens for biological research or medical testing using a solution of formaldehyde. The present invention particularly relates to a method and a composition for chemically controlling the fixation time of such specimens.

BACKGROUND OF THE INVENTION

Fixation is the first important step in preparing cell and tissue specimens for use in a wide range of analytical tests. Some exemplary tests include immunohistochemistry (IHC), flow immunocytometry, in situ hybridization (ISH) with nucleic acid probes, in situ polymerase chain reaction (PCR), and PCR. These tests are typically used to detect particular DNA or RNA sequences, peptides, proteins, or other kinds of biomolecules, drugs, and general analytes.

Fixation stabilizes microscopic cellular structures and compositions in the specimens to allow them to withstand subsequent processing and to preserve them for retrospective analyses. The fixed cell and tissue specimens can also be used to extract biosynthetic molecules for biochemical or nucleotide sequence analysis. Without fixation, it would be difficult, if not impossible, to sensitively detect, localize, and quantitate biosynthetic or environmental molecules in many kinds of cell and tissue specimens.

A good fixative should harden cell and tissue components to prevent decomposition, putrefaction, and autolysis. The physico-chemical process of tissue modification by a fixative is gradual and complex, involving diffusional penetration into the tissue and a variety of potential chemical reactions. To date, no ideal fixative has been found, i.e., a fixative that perfectly preserves cellular morphology and yet does not modify the specimen composition so as not to change the reactivity of the analyte species therein for subsequent detection. Because of this predicament, the selection of a particular fixative generally entails multiple considerations. Thus, there are many fixatives currently in use.

A fixative with a high content of alcohol or other organic solvent, particularly when acidified with a mild organic acid, hardens tissue specimens by precipitation and coagulation. Such a fixative has several advantages. First, since the fixative does not covalently modify the constituent molecules in the tissue, the reactivity of most antigens in the tissue toward antibodies remains very high. Second and for the same reason, nucleic acids in the tissue may be easily extracted in good condition. Third, the fixative may be completely flushed out of the tissue by rehydrating the tissue in a buffered solution.

Such a fixative, however, has one major drawback. The drawback is that the microscopic morphology of an alcohol- or other solvent-fixed tissue is not as detailed as that of a tissue fixed with a covalent-binding fixative.

In contrast to an alcohol- or other solvent-based fixative, a covalent-binding fixative, such as formaldehyde, provides excellent cellular preservation. Formaldehyde ($CH_2O$) was first reported as a tissue preservative by F. Blum in 1893 (10 Z. Wiss. Mikrosc. 314). It is now the most widely used fixative in histopathology because it is cheap, simple to use, and provides consistent results. A formulation of formaldehyde found in most U.S. and foreign research and clinical laboratories is neutral buffered formalin (NBF). It may also be called "buffered neutral formalin." See R. Lillie, *Histopathologic Tech.* 300 (1948). Other formaldehyde formulations include: 10% formalin; alcoholic formalin; calcium acetate formalin; Bouin's Fluid (containing picric acid or acetic acid, pH 1.6); Cajal's formalin-ammonium bromide; formalin/alcohol/acetic acid; paraformaldehyde (polymerized formaldehyde); and formol-saline (G. Clark, *Staining Procedures* 13–16 (1981)).

The commercially available saturated aqueous formaldehyde stock containing 10% methanol stabilizer is called formalin. Its formaldehyde concentration can be denoted in several ways. In particular, it can be denoted as a 100% saturated, a 37% w/w, a 40% w/v, or a 13.3 M solution. A usual working dilution of this stock for fixatives is 1:10 (initial:final) by volume. Such a dilution produces a 10% saturated solution which can also be denoted as 3.7% w/w, 4.0% w/v, or 1.3 M formaldehyde. For example, the standard NBF solution of the U.S. Armed Forces Institute of Pathology Formulation (AFIP) is a 1:10 v:v dilution of formalin in a phosphate buffer at a pH of 6.8 to 7.2 (*Laboratory Methods in Histotechnology* (eds. Edna Prophet et al., 1992)).

The chemistry of aqueous formaldehyde has been thoroughly reviewed, notably in J. Walker's treatise *Formaldehyde*, ch. 8 (1944). Formaldehyde is a gas that rapidly combines with water (>99.9% according to C. H. Fox et al., 33 *J. Histochem. Cytochem.* 845–853 (1985)) to form the hydrate, methylene glycol:

$$CH_2O + H_2O \rightarrow CH_2(OH)_2$$

Methylene glycol can be polymerized by commercial processes to form paraformaldehyde (polyoxymethylene glycol):

$$nCH_2(OH)_2 \rightarrow (CH_2O)_n \cdot H_2O + (n-1)H_2O$$

which is sometimes used instead of formalin in the formulation of formaldehyde fixatives. In a neutral to alkaline buffered solution, paraformaldehyde depolymerizes to methylene glycol which dehydrates into an equilibrium with active carbonyl formaldehyde (Walker, supra, pp. 74–75). Thus, its effect on tissue is the same as diluted formalin.

Methylene glycol rapidly penetrates into tissue by diffusion at a rate that varies inversely with the tissue specimen temperature. Tissue penetration has been measured at 0.5 cm in 8 hours in rabbit liver (W. T. Dempster, 107 *Am. J. Anat.* 59–72 (1960)). Dehydration of methylene glycol within the tissue maintains an effective level of reactive carbonyl formaldehyde. Fixation reactions of carbonyl formaldehyde are much slower than the rate of penetration and are temperature dependent. Thus, when $^{14}C$ formaldehyde was applied to semi-thin (16 μm) tissue sections of rat kidney, the binding reaction took over 24 hours to reach equilibrium (C. H. Fox et al., 33 *J. Histochem. Cytochem.* 845–853 (1985)).

Formaldehyde, which is a very reactive electrophilic species, fixes tissue by combining with proteins and nucleic acids therein (Feldman, 13 *Prog. Nucleic Acid Res. Mol. Biol.* 1–49 (1973)). Formaldehyde modifications of the tissue proceed in two kinetically distinct stages. Initial reactions modify primary amines (lysine) and thiols (cysteine), and purine but not pyrimidine bases of nucleic acids, forming mono- and di-methylol derivatives, not Schiff bases. Regardless of whether the reaction involves nucleotides, nucleic acid polymers, amino acids, or proteins, this stage reaches equilibrium within 24 to 48 hours. These labile adducts are rapidly reversible if the formaldehyde is removed from the tissue.

Subsequent reactions involve the methylol derivatives that are covalently bound in the tissue. These secondary reactions form methylene crosslinks which are not reversible upon washing. In proteins, the secondary crosslinking reaction occurs via methylene bridges that join the first-modified sites to adjacent, less reactive functional groups including primary amides (glutamine, asparagine), guanidine groups (arginine), and tyrosine ring carbons (H. Fraenkel-Conrat & H. S. Olcott, 70 *J. Am. Chem. Soc'y* 2673 (1948)). This reaction is very gradual, accumulating over at least 30 days of fixation, and generates relatively stable covalent crosslinkages. In nucleic acids, secondary reactions also result in chain crosslinking. In addition to chain crosslinking, the reaction can produce crosslinkages between nucleic acids and proteins.

All of these secondary reactions produce a lattice of crosslinkages within and between macromolecules in the fixed tissue. The net effect of all covalent modifications is to partially denature the biopolymers in the tissue by interfering with the normal noncovalent bonding patterns of the charged protein side chains, and to lock the conformation into an inflexible configuration, i.e., the secondary nature of the macromolecules is not changed (Mason et al., 39 *J. Histochem. Cytochem,* 225 (1991)), while the conformation is locked into an inflexible configuration.

These secondary crosslinking reactions have an adverse impact on the analytical tests that are performed on the fixed tissue. For example, selective staining of a macromolecular species (protein, nucleic acid) or a smaller molecule (protein adduct, drug, metabolite, signal transduction species, lipid, etc.) in fixed tissue is often performed using an antibody that binds specifically and with high affinity to the analyte in the tissue. For sequence-specific detection of nucleic acids, a detectable complementary oligo- or poly-nucleotide sequence (probe) can be used for hybridization. Hybridization can be done on intact cell structures (in situ) for cytometric assay (e.g., by microscopy or flow cytometry). However, crosslinkages inside the fixed tissue prevent the large probe molecules employed in these tests, particularly antibodies and oligo- or polynucleotides, from penetrating. Reduced access by these probe molecules translates into loss of assay sensitivity.

Hybridization can also be done on soluble extracts prepared from tissue or cells for a composition assay (e.g., in gels or blots). Fixative modifications can compromise either the extraction efficiency, or the reactivity of the analyte. For example, fixation may affect the extraction efficiency of nucleic acids or the efficiency of subsequent nucleic acid amplification.

Similarly, one of the noncovalent binding forces that causes adhesion of the antibody or probe is the Coulombic attraction between opposite charges which produces hydrogen bonding, i.e., the pairing of oppositely charged groups on the test and analyte molecules. However, side-chain modifications and crosslinkages in the tissue can interfere with the capacity of an analyte to form these noncovalent bonds with an antibody or nucleic acid probe. Thus, it can be seen that formaldehyde modifications of the sulfhydryl and charged amino side chains that are involved in specific noncovalent binding interactions with the applied ligand, are deleterious to assay sensitivity.

A large target analyte such as a protein containing many potential epitopes can be detected using many different antibodies. Different epitopes have different polarity and sensitivity to formaldehyde fixation, presenting a range of susceptibilities to modification. There are many examples of target analytes that are detectable with one antibody, but not with another after extensive formaldehyde fixation. At one extreme, there are many antibodies that can only be used on frozen-sectioned tissue. Some of these can only tolerate a brief post-fixation of tissue in acid alcohol before antibody binding.

With many other antibodies, a progressive loss of antigenic reactivity has been found during prolonged formaldehyde fixation. The widely expressed cancer marker protein p53, for example, gradually loses all of its reactivity toward monoclonal antibody PAb1801 when fixed in formaldehyde for between 6 and 24 hours (R. Silvestrini et al., 87 *J. Nat. Cancer Inst.* 1020 (1995)). Similarly, the diagnostically important epithelial cell marker protein keratin gradually becomes unable to bind with a monoclonal anti-keratin antibody if the tissue is fixed in formaldehyde for up to 24 hours (H. Battifora & M. Kopinski, 34 *J. Histochem. Cytochem.* 1095–1100 (1986)).

There are other antibodies that are effective on tissue fixed for one day, but are less effective on tissue stored in NBF for longer periods. Some of these antibodies which are commonly employed in tumor diagnosis include lymphocyte antigens, vimentin, desmin, neurofilaments, cytokeratins, S100 protein, prostate specific antigen, thyroglobulin, and carcinoembryonic antigen (A. S. Leong & P. N. Gilham, 4 *Pathology* 266–268 (1989)). Other examples of such antibodies can be found in the biomedical literature.

Thus, it is important to control the tissue fixation time to achieve a compromise between the preservation of tissue morphology and the loss of antigenicity. As a general rule, the duration of aldehyde fixation should be kept to a minimum so as to allow the specimen to be tested using a wide range of different antibodies.

The quality and reproducibility of immuno-assay results also depend on the fixation time of the tissue. Currently, fixation is terminated by physically exchanging alcohol for the fixative solution. Leong and Gilham recommend fixing surgical histopathology specimens for no more than 6 hours. According to them, surgical pathology specimens are usually sampled after being fixed for 4 to 24 hours. However, in practice, the bulk of the surgical resection is often retained in formaldehyde for future resampling, which may occur after 3 or more days.

Autopsy specimens are usually fixed for between 3 and 14 days, depending on convenience. However, under some circumstances, it may not be expedient for laboratory personnel to closely monitor the specimens to achieve a preferred fixation time. These personnel may be occupied with other business and thus be absent when the fixative solution should be removed.

In addition, a biopsy or postmortem specimen that is not processed in-house may be sent to a pathology laboratory in a fixative. This transportation time often adds to the total fixation time of the specimen. Also, a specimen that arrives on Friday may not be processed until after the weekend, thereby extending the total fixation time even longer.

Moreover, a laboratory technician may accumulate many specimens for batch processing rather than separately process each sample after a predetermined fixation time. Thus, accurate records of the total fixation time of each individual sample may not be available for later reference for quality control standardization.

Variable staining is common when IHC is applied to archival paraffin-sections which were fixed for an unknown period of time. Such variations can be a "hidden variable" that confounds retrospective research experiments on the expression of putative cancer marker proteins that are fixation-sensitive such as the most widely expressed cancer marker protein p53 (P. Hall & D. Lane, 172 *J. Pathol.* 1–4 (1994)).

An important issue relating to histopathologic applications of immunologic and genetic tests is their reproducibility and quality. Recently, the College of American Pathologists and several other groups petitioned the Food and Drug Administration (FDA) to classify the nearly 2,500 antibodies sold in the U.S. as Class II medical devices (R. Stone, 268 *Science* 494 (1995)). The FDA has announced its intention to classify certain IHC reagents as Class II or Class III medical devices. This would require manufacturers to document the accuracy and precision of the tests (C. Graziano, 10 Col. *Am. Pathologists* 1 et seq. (1996)). Thus, both the FDA and the pathologists in the field recognize a need for better quality control and greater standardization of immunohistochemical procedures.

Fixation-induced loss of target epitopes can be compensated for by using several techniques, which have been termed antigen "retrieval," "restoration," "un-crosslinking," or "unmasking" in the literature. These techniques are performed on thin tissue sections which are individually processed. However, these techniques do not necessarily remedy the loss of standardization owing to uncontrolled variations in fixation and remediation. Variable fixation time requires a variable and unknown amount of uncrosslinking/unmasking to reach the same level of immunoreactivity, if in fact immunoreactivity is not irreversibly lost.

A number of antigens concealed by formaldehyde fixation can be re-exposed by applying protease solution to the tissue section (S. Huang et al., 35 *Lab. Invest.* 383 (1976); H. Battifora & M. Kopinski, 34 *J. Histochem. Cytochem.* 1095–1100 (1986)). However, more prolonged exposure to formaldehyde necessitated more vigorous proteolysis so as to recover a constant level of immunoreactivity. Proteolysis must be minimized because extensive protease digestion degrades the tissue morphology. In practice, the length of formaldehyde exposure could vary in different samples, suggesting the impracticality of standardizing the proteolysis time. Different antigens require different protease treatments. Therefore, this is not a simple way to address standardization concerns.

Microwave antigen retrieval was disclosed by M. E. Key, S. R. Shi, and K. L. Kalra in U.S. Pat. No. 5,244,787 (Sep. 14, 1993) and in S. R. Shi et al., 39 *J. Histochem. Cytochem.* 741–748 (1991). The method involves boiling the tissue section on a microscope slide in an aqueous solution selected from various defined pH and ionic compositions. Bankfalvi et al., 174 J. Pathol, 223–228 (1994) found that an equally effective and more expedient method was to autoclave hydrated sections. Recent developments of a variety of novel methodologies are summarized in a review by S. R. Shi, R. J. Cote & C. Taylor (45 *J. Histochem. Cytochem.* 327 (1997)), in which the need in this field for better optimization and standardization is stressed.

Cattoretti et al., 171 *J. Pathol.* 83–98 (1993) compared proteolysis to microwaving in various solutions. They found that some antigens benefit selectively from either one of the treatments, but not from both. The authors inferred that the common mechanism of antigen unmasking methods was related to protein denaturation. However, there was no obvious pattern relating the amino acid composition of particular protein epitopes to the deleterious effects of formaldehyde on their subsequent detectability by immunostaining with different monoclonal antibodies. Consistent with the findings of others in the field (S. R. Shi et al., 39 *J. Histochem. Cytochem.* 741–748 (1991); A. S. Leong & P. N. Gilham, 4 *Pathology* 266–268 (1989)), these authors found that some, but not all epitopes can be fully recovered after over-fixation, either by proteolysis or by heating. Because some fixation-sensitive antigens exist for which antigen retrieval is not effective, and because other fixation-sensitive antigens exist which may benefit from antigen retrieval only if they are overfixed, these differences give rise to a need in the art for a definitive method and composition that would standardize the extent of antigen masking by standardizing the fixation time.

DNA content can be measured in single cells in formalin fixed paraffin embedded tissues, or in cells recovered therefrom, to assay for cell proliferation by image analysis or flow cytometry. Formalin over-fixation interferes with the measurement of DNA content by decreasing the binding of propidium iodide and other fluorescent DNA-binding dyes, probably because it makes crosslinked DNA-histone complexes. Thermal antigen retrieval was applicable to this problem using cell suspensions or tissue sections (W. R. Overton & J. P. McCoy, 16 *Cytometry* 351–356 (1994); W. R. Overton & J. P. McCoy, 26 *Cytometry* 166–171 (1996)).

DNA or RNA can be extracted from formalin fixed, paraffin-embedded tissue samples for genetic analysis. These can be quantitated and then amplified using the PCR to determine the presence of a gene sequence such as for expression or mutation analysis. Formalin-fixed paraffin embedded tissue was only amenable to PCR sequence analysis if the tissue was fixed in NBF for approximately 12–24 hours (J. J. O'Leary et al., 26 *Histochem. J.* 337–346 (1994); C. E. Greer et al., 95 *Am. J. Clin. Pathol.* 117–124 (1991); F. Karlsen et al., 71 *Lab. Invest.* 604–611 (1994)). PCR in situ/in situ PCR methods are used for genetic analysis of archival, formalin-fixed paraffin embedded tissues, for example, to detect viruses and oncogene mutations in single cells. Limited fixation of 24–48 hours gave the best in situ amplification results (J. J. O'Leary et al., 26 *Histochem. J.* 337–346 (1994)). Thus, over-extended periods of fixation can adversely effect the results of these types of tests as well as others mentioned above.

Quantitative variations in tissue formaldehyde conjugation are difficult to assess retrospectively in IHC procedures. Battifora proposed that a partially fixation-sensitive antigen that is subject to a gradual loss of immunoreactivity in proportion to the extent of fixation in NBF could serve as an internal control. Battifora, in 96 *Am. J. Clin. Pathol.* 669–671 (1991), proposed to calibrate the average decrease of antibody binding in a fixed tissue by staining a section for a "universal surrogate epitope" for which he proposed using the ubiquitous endothelial marker vimentin. However, this method does not directly address the need for standardized fixation for total quality control.

In view of the above, there is a need in the art for a method and a composition that would prevent the secondary crosslinking reactions from occurring without the need to physically remove the cell or tissue specimen from the fixative solution or without the need to closely monitor the fixation time of the specimen or both. There is also a need in the art for a method and a composition that would allow for economical batch processing of cell or tissue specimens in a fixative while at the same time standardizing the fixation time of those specimens without the need for close supervision. There is a further need in the art for a method and a composition that would make analytical testing methods such as IHC and ISH more sensitive and consistent by raising the level of quality control as regards the tissue fixation time without a high economic cost.

Accordingly, it is an object of the present invention to provide for a method and a composition for preventing the secondary crosslinking reactions from occurring without the need to physically remove the tissue from the fixative solution or without the need to closely monitor the fixation time of the tissue specimen or both. It is a further object of the present invention to provide for a method and a composition that would allow for the economical batch processing of cell or tissue specimens in a fixative while at the same time standardizing the fixative time of those specimens without the need for close supervision. It is a further object of the present invention to provide for a method and a composition that would standardize an important variable in the fixation of tissue specimens, i.e., the time of fixation with formaldehyde.

These and other objects of the invention will be more readily understood by reference to the following summary, detailed description, and the appended drawings.

SUMMARY OF THE INVENTION

The present invention achieves all of the foregoing objects and solves the problems associated with over-fixation of cell and tissue specimens. Those problems include the formation of undesired methylene crosslinkages and the loss of antigenic activity. The present invention solves these problems by providing methods and compositions for controlling formaldehyde fixation of a biological sample by quenching the fixative with a formaldehyde-reactive agent.

In one of its composition aspects, the present invention is directed to a composition comprising a formaldehyde-reactive agent and an effervescent agent.

In another of its composition aspects, the present invention is directed to a composition comprising a core and a coating layer around the core. The core comprises a formaldehyde-reactive agent.

In one embodiment, the formaldehyde-reactive agent is urea. In another embodiment, the formaldehyde-reactive agent is an ammonium salt.

The present invention further relates to a kit of parts. In one of its kit aspects, the present invention is directed to a kit comprising at least one of the above-mentioned compositions and a volumetrically calibrated container for biological tissue fixation.

In another of its kit aspects, the present invention relates to a kit of parts comprising at least one of the above-mentioned compositions and at least one ancillary composition for neutralizing the pH of the fixative. The ancillary composition includes a core and a coating layer around the core. The core comprises an additive to neutralize the pH of the fixative.

In one of its method aspects, the present invention is directed to a method for quenching a fixative comprising formaldehyde. The method comprises contacting the fixative with at least one of the compositions mentioned above.

In another of its method aspects, the present invention is directed to a method for fixing a biological sample. The method comprises contacting the sample with a fixative comprising formaldehyde. The method further comprises contacting the fixative with at least one of the above-mentioned compositions.

In yet another of its method aspects, the present invention relates to a method of regulating the exposure of a biological sample to a fixative reagent. The method includes exposing a biological sample to a fixative reagent for a predetermined amount of time. The method further includes contacting the fixative reagent and the biological sample with an amount of fixative quenching reagent sufficient to substantially stop the fixation of the biological sample.

In a further aspect, the present invention relates to a biological sample made by the above-mentioned methods.

BRIEF DESCRIPTION OF THE DRAWINGS

FIGS. 1A and 1B show a tissue sample that was fixed with a neutral buffered formaldehyde (NBF) for 18 hours and then placed in ethanol for 29 days.

FIG. 1C shows a tissue sample that was kept in NBF for 30 days.

FIG. 1D shows a tissue sample that was fixed in NBF for 18 hours and then quenched with an equimolar amount of urea and stored for another 29 days.

DETAILED DESCRIPTION OF THE INVENTION

Figure 2A:
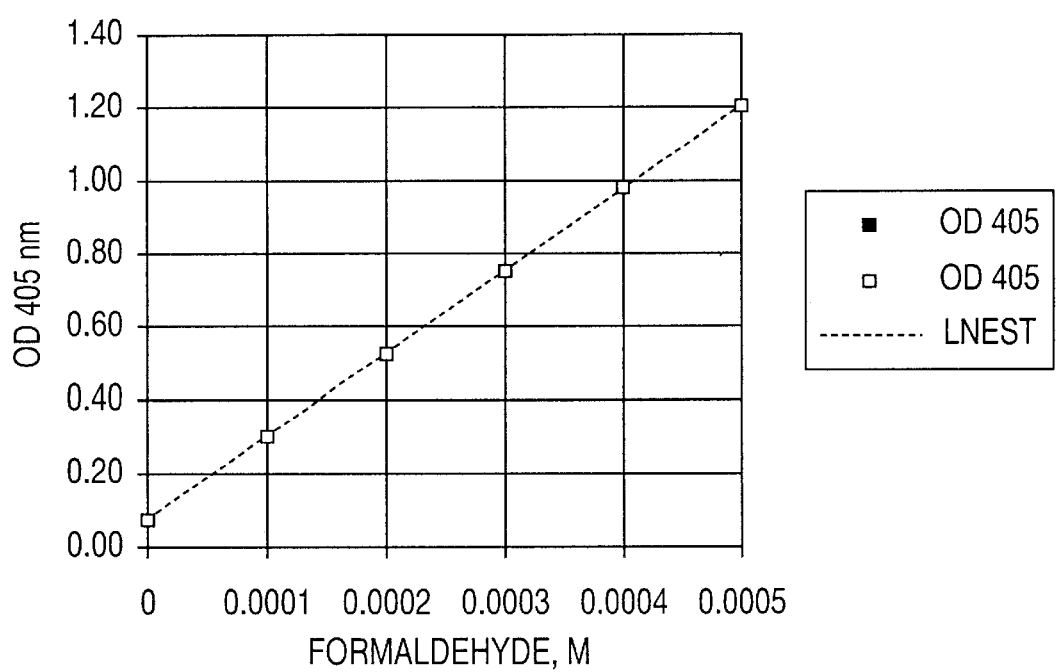
FIG. 2A shows the calibration of an assay for formaldehyde by reaction with acetylacetone, using dilutions of NBF as standards.

The present invention is generally directed to methods and compositions for controlling the formaldehyde fixation of a biological sample by quenching the fixative with a formaldehyde-reactive agent. However, prior to discussing the invention in detail, the following terms will first be defined:

The term "tablet" means a cohesive mass. A tablet typically, but not always, comprises a powder which has been compressed into a cohesive solid.

The term "capsule" is used to describe a system by which a solid or liquid material is enclosed by an external restraint. A capsule typically, but not always, comprises of a powder or liquid placed in a capsule shell which is usually made of gelatin.

The term "coating layer" is used to describe a layer that is applied to the outer surface of a delivery system. This layer typically, but not always, is designed to alter the diffusion rate of the active ingredients enclosed within the coating layer or to protect the active ingredients from various environmental factors which adversely affect the active ingredients.

The present invention has several aspects. In a first aspect, the present invention is directed to a composition for quenching a fixative comprising formaldehyde. The quenching composition comprises a formaldehyde-reactive agent and an effervescent agent.

This composition can be in the form of an uncoated tablet. The uncoated tablet allows for the formaldehyde-reactive agent to disperse immediately upon contact with the fixative, upon which the formaldehyde-reactive agent will begin to react with and quench the fixative action of the formaldehyde. The uncoated tablet according to the present invention allows for a method of quenching the fixative without physically removing the biological sample or changing the bathing solution.

The formaldehyde-reactive agent can be any chemical that meets the following criteria: (1) dissolves in water at room temperature or below within about an hour to a concentration of at least about 0.25 M; (2) reacts with formaldehyde in an aqueous solution at about a neutral pH and at room temperature or below to form a compound or compounds that are stable and relatively unreactive toward tissue constituents; (3) does not cause a large drop or rise in the solution pH; (4) is not more than slightly corrosive, toxic, irritating, or carcinogenic; and (5) can be incorporated into a tablet, pellet, or capsule.

In one embodiment, the formaldehyde-reactive agent is urea (carbamide; carbonyl diamide; or $H_2NCONH_2$). It has all of the requisite properties mentioned above. Urea is highly soluble in water and is very reactive with formaldehyde at a neutral pH (7.2–7.6) at room temperature or below. Importantly, the reaction between urea and formaldehyde does not change the pH of the fixative solution. Urea as well as the compounds formed by its reaction with formaldehyde are not reactive with tissue constituents such as proteins and nucleic acids. Urea is noncorrosive, nontoxic, noncarcinogenic, nonirritating, and nonodorous. Finally, it is amenable to compressive formulation and surface coating as a tablet.

As mentioned above, urea rapidly condenses with formaldehyde in aqueous solution at a neutral pH and room temperature (J. F. Walker, *Formaldehyde* 110, 208–209 (1944)). When an equimolar ratio of reactants is used, the reaction product is monomethylol urea:

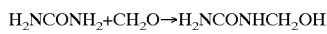

At a molar ratio of 1:2, the reaction product formed is dimethylolurea:

The equilibrium residue concentration of formaldehyde is relatively high at a molar ratio of 1:2. Therefore, a urea to formaldehyde molar ratio of about 1:1 to about 2:1 is preferred.

Preferably, anhydrous, ultra-pure grade urea is used as the formaldehyde-reactive agent in the composition of the present invention. The composition may be stored in a blister-type package. Alternatively, it could be stored in a dispenser comprising a desiccator.

In one embodiment, the formaldehyde-reactive material is an ammonium salt. The ammonium ($NH_4^+$) salts, are highly soluble in water, and are a conveniently concentrated and stable source of the ammonia ($NH_3$) molecule. Ammonia is very reactive with formaldehyde at a neutral pH (about 7.2–7.6) at room temperature or below. The rapid rate of a reaction of formaldehyde with an exemplary ammonium salt is shown in Example 17, FIG. 5.

Ammonium salts typically do not react significantly with tissue constituents, such as proteins and nucleic acids. Most of the ammonium salts are generally noncorrosive, nontoxic, noncarcinogenic, and have a very mild odor. Some ammonium salts, more than others, are amenable to compressive formulation as a tablet, and to application of a uniform surface coating to the tablet. Examples of ammonium salts include, but are not limited to ammonium bicarbonate, ammonium hydrogen phosphate, ammonium benzoate, ammonium alginate, ammonium bitartrate, ammonium citrate, dibasic, ammonium chloride, ammonium gluconate, ammonium velerate, ammonium thiocyanate, ammonium phosphate, monobasic, ammonium acetate, ammonium nitrate, ammonium sulfate, ammonium sulfamate, ammonium purpurate, ammonium tartrate, ammonium hippurate, ammonium iodide, ammonium bromide, ammonium fluoride, ammonium carbonate, ammonium citrate, ammonium acetate and the like.

The principal reaction product of ammonia and formaldehyde is hexamethylenetetramine (1, 3, 5, 7-tetraazatricyclo[3.3.1.1$^{3,7}$]-decane; synonyms: HMTA, methenamine, hexamine) [100-97-0] ($C_6H_{12}N_4$; F.W. 140.2; Merck Index 11th edition, 1989, monograph #5879). HMTA is a stable, highly water-soluble, weakly basic tertiary amine-containing compound of adamantine-like structure.

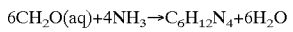

The formation and properties of HMTA are described in J. F. Walker's treatise (*Formaldehyde*, Reinhold, N.Y., 3rd edition, 1964, chapter 19, pp. 511–551). The reaction is rapid (FIG. 5), and consumes at least about 90% of the formaldehyde when equal moles of ammonium and formaldehyde are reacted.

Tissue shrinkage during fixation could cause a problem for the exact measurement of microscopic structures in a tissue. Therefor, moderation of the fixative osmotic strength is beneficial as regards the avoidance of tissue shrinkage during fixation. Incorporation of six mole equivalents of carbon and four mole equivalents of nitrogen per one mole of HMTA confers a lowering of total osmotic strength that substantially offsets the osmotic strength of the added ammonium salts and excipients.

The pH of the reaction is a variable that modifies the fraction of available ammonium ion that is reacted. In order to effect a nearly quantitative reaction, the reaction should be buffered to pH in the range of at least about 6.7 to about 7.0. As ammonia, and not ammonium, is the reactant species, hydrogen ions (H$^+$) are imparted to water and so the pH tends to decrease during the reaction.

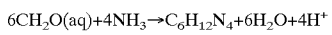

This reaction normally can impart $^2/_3$ mole of hydrogen ions per mole of formaldehyde reacted. The NBF contains phosphate buffer, usually at bout 0.075 M, which is much lower than the concentration of formaldehyde to be reacted, which is 1.3 M. Since this reaction would tend to lower the pH of the fixative solution, a buffer can be provided to neutralize the reaction pH. In a preferred aspect, the buffer is an intrinsic constituent in the formaldehyde reactive agent. In this manner, the tablet content and the difficulty of fabrication is minimized. Thus, the anion of the ammonium salt can function as the buffer.

A direct comparison of seven different ammonium salts shows that the pH is strongly associated with the residual formaldehyde concentration, particularly below neutrality. When bicarbonate or carbonate is added to the quenching reaction of ammonium, the pH is raised and the reaction goes farther toward completion (Example 18).

In the fabrication processes used for making tablets and, optionally, coating them, certain difficulties can be proportional to the tablet bulk. However, it is preferred that tablets of the largest feasible size would be used to quench larger volumes of fixative. Use of ammonium bicarbonate as an intrinsic buffer of the reactive ammonium salt is economical and efficient, because it reduces the use of material as compared to using one ammonium salt and one ancillary buffer. Thus, a preferred composition of the invention includes ammonium bicarbonate as a primary buffering agent. It should be understood, however, that the composition can include other known buffering agents.

Examples of other formaldehyde-reactive agents which can be incorporated in accordance with the present invention are amino acids such as glycine and derivatives thereof such as glycine ethyl ester hydrochloride, alanine, asparagine, etc.; proteins such as collagen, gelatin, casein, etc.; urea hydrogen peroxide (carbamate peroxide); thiourea; carbamic esters (urethanes); cyanamide, dicyanamide, and melamine; sodium bisulfite; hydrogen sulfide; sugars such as fructose and glucose in alkaline solution; malonic ester; phenylhydrazine; aniline; solid hydrazines dihydrochlorides, hemisulfates, sulfate, (acidifiers) and hydroxylamines (acidifiers).

The amount of formaldehyde-reactive agent used can vary depending on the amount of formaldehyde required to be quenched and the desired size of the composition itself. In total, the molar ratio of the formaldehyde-reactive agent to formaldehyde should be between about 0.8:1 to about 2:1 and should preferably range from about 0.8:1.0 to about 1.5:1.0. Preferably, the amount of formaldehyde-reactive agent employed is such that it leaves a residual formaldehyde concentration of about 0.25 M or less in the fixative solution. The residual formaldehyde concentration serves the purpose of both maintaining the level of fixation in the treated tissue and suppressing any decay- or disease-causing microorganisms.

The effervescent agent in the composition speeds up dissolution and dispersal of the formaldehyde-reactive agent upon contact with water in the fixative solution. Any effervescent agent known in the art may be used in the composition of the present invention. Typical effervescent agents include a combination of a mild organic acid and a carbonate compound. Exemplary mild organic acids include citric acid, tartaric acid, malic acid, fumaric acid, adipic, and succinic acid. Exemplary carbonate compounds include sodium carbonate, sodium bicarbonate, potassium carbonate, potassium bicarbonate, sodium sesquicarbonate, sodium glycine carbonate, L-lysine carbonate, arginine carbonate, and amorphous calcium carbonate. These materials may be mixed and manufactured using techniques known in the art. For example, see *Pharmaceutical Dosage Forms: Tablets,* Vol. 1 by H. A. Liberman, L. Lachman, and J. B. Schwartz (Marcel Dekker, New York, N.Y.).

In a preferred embodiment of the invention, the ammonium ion functions as the intrinsic mild organic acid by releasing a proton in the reaction with formaldehyde fixative. Thus, a preferred effervescent carbonate compound in the method and composition of the invention is the intrinsic bicarbonate anion of the ammonium salt.

$$4NH_4HCO_3 \rightarrow 4NH_4^+ + 4HCO_3^- (aq)$$

$$6CH_2O(aq) + 4NH_4^+ \rightarrow C_6H_{12}N_4 + 6H_2O + 4H^+$$

$$4H^+ + 4HCO_3^- \rightarrow 4H_2CO_3 \rightarrow 4CO_2(gas) + 4H_2O$$

Use of an intrinsic bicarbonate anion of the ammonium salt, as contrasted with a reactive ammonium salt, an ancillary mild acid, and an ancillary bicarbonate salt, provides a more economical and efficient use of material, which reduces the cost, bulk, and difficulty of fabrication of the composition.

The carbon dioxide gas released by the reaction with formaldehyde may cause pressure to build in a closed container of fixative. Gas pressure could cause leakage, spillage or even rupture of a closed container. Two measures can be utilized to mitigate this potential hazard. One of the measures is to package the fixative in a container with a vent that is permeable to gas but is impermeable to water. Methods of venting containers are well known to those with skill in the art.

Alternatively, the volume of gas released in the reaction can be reduced to benign levels, by replacing a portion, but not all, of the ammonium bicarbonate with a second ammonium salt. The second ammonium salt should have a nearly neutral to alkaline intrinsic pH, and adequate buffering capacity around neutral pH. Examples include ammonium phosphate dibasic and diammonium phosphate. In the preferred composition, the mixture of ammonium salts comprises ammonium bicarbonate ($NH_4HCO_3$, F.W. 84.0) and ammonium hydrogen phosphate (dibasic; $(NH_4)_2HPO_4$; F.W. 132.1).

Different ammonium salts have distinctive physical textures, consistencies, and hygroscopicities. These properties may affect the potential usefulness of different ammonium salts for purposes of formulating and compacting a tablet, regardless of their usefulness as a formaldehyde-reactive agent, buffer or effervescent agent. For example, although ammonium acetate can be used in according with the present invention, it is very hygroscopic and, under normal humidity conditions, it would likely absorb a weight fraction of atmospheric water. Thus, the water content of a formulation of ammonium acetate may be difficult to control during the fabrication of a tablet, and the dry tablet may be relatively unstable. As a further example, although ammonium borate can also be used in accordance with the present invention, it is relatively difficult to compress into a cohesive tablet because of its relatively smooth, coarsely granular consistency. Furthermore, ammonium borate may be less soluble in fixative solution than required. The two ammonium salts preferred in the composition of the invention, ammonium bicarbonate and ammonium phosphate, are non-hygroscopic but water soluble, and when properly formulated together with excipients, they are amenable to compression into a cohesive and stable tablet.

A preferred composition of the formaldehyde reactive agents incorporates a mixture of ammonium salts containing in the range of about 80:20 to about 60:40 mole ratio of starting bicarbonate ion to starting phosphate (dibasic) anions. This is equivalent to a range of about 4:1 to about 1.4:1 mole ratio of $NH_4CHO_3$: $(NH4)_2HPO_4$, respectively. Use of these ratios of these agents imparts a pH after the reaction in the acceptable range of pH about 6.7 to about 7.3, provided that the reaction is run using at least about a 1:1 ratio of moles of ammonium ion to moles of formaldehyde (Example 18).

Use of a composition including ammonium salt for formaldehyde quenching in accordance with the present invention should preferably not substantially alter the pH of the fixative solution. Alternatively, the composition may be modified so as to raise or lower the pH of the fixative. For the purpose of reacting most of the formaldehyde at a lower pH, the mole ratio of formaldehyde reactive agent to formaldehyde should be increased. The reaction pH can be modified by using any ancillary buffer and/or any intrinsic anion of an ammonium salt. Preferably, the reaction pH can be modified most economically by using a different mixture of formaldehyde-reactive agents selected from the class of ammonium salts.

Preferably, all chemicals used in the composition of the invention should be anhydrous before formulation, and of ACS grade or better. The composition may be stored in a blister-type package. Alternatively, it may be stored in a dispenser including a desiccator.

In one embodiment, the quenching composition comprises a core and one or more coating layers around the core. The core includes one or more of the formaldehyde-reactive agents described above. Preferably, the composition is in the form of a coated tablet or a capsule. Any method known in the art can be used to make the coated tablet or capsule.

A typical tablet formulation for the core includes a filler/binder, lubricant and one or more active ingredients. The active ingredient is preferably present in an amount ranging from about 50 to about 75% by weight. The filler is preferably present in an amount ranging from about 20 to about 48% by weight. The lubricant is preferably present in an amount ranging from about 2 to 5% by weight. Examples of suitable fillers include microcrystalline cellulose, dextrose, lactose and mannitol. Examples of suitable lubricants include sodium lauryl sulfate, sodium benzoate, polyethylene glycol (PEG 8000), magnesium stearate, and sodium stearyl fumarate.

The tablets and/or capsules can be manufactured according to generally accepted manufacturing practices. For example, the active ingredient(s) and filler are first blended in a suitable blender for a sufficient time to ensure complete mixing. The lubricant is then added to the mixture and blended for a suitable time, e.g., 5 minutes. Tablets can be formed by compression using a standard tablet press and tablet press tooling.

The coating layer(s) can either serve to protect the core from premature decomposition due to contact with atmospheric moisture or to provide for a delayed release profile or both. Thus, depending on the purpose of the coating layer(s), the layer(s) can vary in thickness as well as in composition.

If a delayed release profile is desired, the coating layer(s) should prevent immediate wetting of the core contents upon contact with the fixative solution. However, when water reaches the core, the coating layer(s) should rapidly break apart and dissolve in the fixative solution or leave an empty coating shell which can be easily removed from the fixative solution. Thus, the coating layer(s) should be of a material and thickness such that it releases the formaldehyde-reactive agent in the core at a desired time to react with the formaldehyde fixative and stop the fixation of the tissue specimen.

Preferably, the coating layer(s) is impermeable to water from about 1 minute to about 36 hours, as measured at room temperature. Room temperature measurements translate into faster effectiveness at higher temperatures, and slower effectiveness at lower temperatures. The particular time in which the coating layer(s) should release the formaldehyde fixative depends on the specimen being fixed because different specimens undergo diffusional permeation by fixative at different rates, and different analytes in the tissue undergo crosslinking at different times of fixation.

Exemplary coating layer materials suitable for use with the present invention include natural, synthetic, or modified natural polymers. Examples of these polymers include dimethylaminoethyl methacrylate, methylacrylate acid ester copolymer, ethylacrylate-methylmethacrylate copolymer, hydroxypropyl methylcellulose, hydroxypropylcellulose, hydroxyethylcellulose, methylcellulose, ethylcellulose, sodium carboxymethylcellulose, polyvinyl pyrrolidone glycol, cellulose acetate phthalate and polyethylene glycol. Other examples include shellacs, silicone elastomers, waxes, and fats. As is well known in the art, these materials are often used with plasticizers such as polyhydric alcohols, acetate esters, phthalate esters, and glycerides. These coating materials can be applied using methods known in the art. For example, see *Pharmaceutical Dosage Forms: Tablets*, Vol. 3, by H. A. Lieberman, L. Lachman, and J. B. Schwartz (Marcel Dekker, New York, N.Y.). The preferred coating layer materials are polymethacrylate polymers, ethyl cellulose and poly(ortho ester) polymers. The polymethacrylate polymers are preferably used in combination with an ammonia methacrylate copolymer.

In one embodiment, the tablet includes a core surrounded by a first layer which may be designated as a subcoating. The subcoating can be used to protect any moisture sensitive materials during application of any subsequent coating layers. The subcoating material may be formulated to include a coating agent such as hydroxypropylmethylcellulose, hydroxypropylethylcellulose, povidone, shellac, maltose/dextrin and the like; a plasticizer such as polydextrose, lecithin, polyethylene gylcol, glycerin, triethyl citrate, triacetin and the like; and may optionally contain adjuvants such as suspending agents which can include alginates, bismuth, carageenan, acacia, tragacanth, lecithin and the like. A commercially available product which is well suited for use in formation of a subcoat is OPADRY™, commercially available from Colorcon, Pa., which is made of hydroxypropylmethylcellulose, polyethylene gylcol, polydextrose, sodium alginate, lecithin and triacetin.

When the formaldehyde-reactive agent is urea and when the composition is coated with a polymethacrylate polymer, it is preferred that the composition further comprise a mild organic acid. Typically, polymethacrylate polymers are used for sustained release, i.e., they are designed to slowly release a drug over an extended period of time. However, the incorporation of a weak acid into the composition accelerates the release rate once water has passed through the coating layer and wetted the core. This was disclosed by Narisawa et al. in 11 *Pharm. Res.* 111–116 (1994). Suitable acids for this purpose include citric acid, tartaric acid, malic acid, fumaric acid, acetic acid, glutaric acid, and succinic acid. Preferably, the mild organic acid is succinic acid. The aforelisted acids are examples of agents which function as disolution aids.

At a neutral to alkaline pH, the reaction product of urea and formaldehyde is soluble in the fixative solution. However, after several days, a thin layer of white precipitate develops and coats contacting surfaces.

At very low pH values, insoluble poly-condensation products, or resins, are precipitated. To avoid the problem of resin formation, the core of the quenching composition can optionally contain a compound that neutralizes the pH of acidic fixatives. The neutralizing compounds can be a base or a buffer. For example, the core of the quenching composition can contain dibasic sodium phosphate to neutralize Bouin's solution.

In a preferred embodiment, when a coated tablet is placed in a formaldehyde fixative solution, there is a planned delay, after which the fixative solution should begin to enter into and react with the tablet core. A small volume of pressurized $CO_2$ gas is initially produced and confined inside of the still intact tablet coating. Release of a sufficient amount of this gas subsequently causes an abrupt rupture of the residual coating of the tablet as evidenced by the observation that the coating was torn open and shed from the tablet in one piece. Thus, in accordance with the present invention the coating pops open and causes rapid exposure of the core contents in a single burst, to clearly define the time when the quenching of formaldehyde begins.

The composition may also be coated with water soluble polymers such as a polymethacrylate type polymer or cellulose acetate phthalate. When these coated tablets are placed in a formaldehyde fixative solution, the polymer begins to hydrate and dissolve. Eventually, after a period of time, enough of the polymer has dissolved so that the structural integrity of the coating is diminished to the point where the core will be rapidly exposed to the fixative solution. The rapid exposure of the core is facilitated by the effervescent nature of the core.

Thus, a preferred composition of the invention includes the bicarbonate salt of ammonium which causes a burst release of the formaldehyde reactive agent from the coating, acts as an intrinsic buffer, is the main active species in the reaction with formaldehyde and acts as the effervescent agent.

Since there is a limit to the potential size of the quenching composition, a second, separate coated composition comprising only the neutralizing compound and excipients in its core can be used in conjunction with the quenching composition. Of course, use of the second composition would be ancillary to the use of the quenching composition.

The coating layer of the second/ancillary composition can be made of the same material as the coating layer of the quenching composition. It can also be made of a different material. Preferably, the coating layer of the second/ancillary composition has a shorter delayed release profile than the coating layer of the quenching composition. This will allow the neutralizing compound in the second/ancillary composition to neutralize the pH of the fixative before the quenching composition releases the formaldehyde-reactive agent.

Naturally, depending on the pH and temperature of the fixative solution, the coating layer material of the quenching composition as well as the second/ancillary composition can vary so as to achieve a desired delayed release profile.

As noted above, the quenching reaction of urea with formaldehyde is temperature dependent as well as pH dependent. For example, the quenching reaction of urea with formaldehyde is 10 times slower at 4° C. than at 24° C. See FIG. 2B. At such temperatures, the total time of quenching is about 24 hours. Thus, when a sample is fixed with formaldehyde at low temperatures, it is not necessary to use a quenching composition with a delayed release profile, i.e., it is not necessary to use a coated tablet or capsule to deliver the urea. The urea composition containing an effervescent agent may be delivered directly into the fixative solution and at the same time that the sample is placed in the fixative. At which point, both fixation and quenching will be taking place.

The quenching reaction of ammonium salts with formaldehyde is temperature dependent as well as pH dependent. For example, the quenching reaction of ammonium acetate with formaldehyde is 3 times slower at 4° C. than at 24° C. See FIG. 5.

Since the quenching reaction of formaldehyde reactive agent with formaldehyde is temperature dependent, it is contemplated that the quenching composition of the present invention may have coating layers with varying thicknesses. The thickness of the coating layer would be dependent on the temperature of the fixative solution. Moreover, even though the quenching composition of the present invention may be used without a coating layer, it is preferred that the quenching composition have a thin coating layer thereon simply to protect the formaldehyde-reactive agent from degradation and deterioration by atmospheric moisture.

In one aspect, the present invention is directed to a kit of parts. The kit comprises at least one of the formaldehyde-quenching compositions described above and a volumetrically calibrated container in which a tissue sample can be fixed. The container is designed to measure out a specific amount of the formaldehyde fixative solution that can be quenched with the packaged quenching composition or compositions. Optionally, the container is prefilled with the specific amount of the fixative solution.

The kit makes it expedient for the user to use a defined molar ratio of formaldehyde-reactive agent to formaldehyde, which is preferably from about 0.8:1 to about 2:1. The amount of the formaldehyde-reactive agent in the quenching composition provided in the kit should be sufficient to make at least a 1.3 M solution in a defined volume of water.

Because different tissue specimens require different amounts of formaldehyde to effect fixation as well as different times until quenching, it is contemplated that the kit will have different sized containers and quenching compositions with varying dosages of the formaldehyde-reactive agent. More than one quenching composition can also be used to quench one large volume of fixative. Preferably, two or more quenching compositions are used to quench one large volume of fixative. In addition, the quenching compositions in the kit can have different delayed release profiles depending on the specimen to be fixed.

Formulations of the present invention that incorporate an effervescing compound would cause gas pressure to build up inside of a non-vented container. Therefore, the preferred kit design of the present invention has a container with a close-fitting lid. The lid can be fitted with a vent in which a small, semipermeable membrane filter is mounted. The filter may be a hydrophobic microporous membrane type, which allows for venting of over-pressure gas, but which retains water and gas at normal atmospheric pressure. For example, it may be composed of any of these materials: polytetrafluoroethylene (PTFE; Gore-Tex®), polypropylene, acrylic copolymer, or polyvinyl difluoride (PVDF).

In another of its kit aspects, the present invention is directed to a kit of parts comprising at least one of the formaldehyde-quenching compositions mentioned above and at least one of the second/ancillary compositions described above. In particular, the second/ancillary composition includes an ancillary core and an ancillary coating layer around the ancillary core. The core comprises an additive to neutralize the pH of the fixative solution. The core optionally contains a formaldehyde-reactive agent for quenching the fixative as well. Its other embodiments can be the same as the aforementioned kit aspect of the present invention.

In one of its method aspects, the present invention is directed to a method for quenching a fixative comprising formaldehyde. The method comprises contacting the fixative with at least one of the above-described quenching compositions.

Various formaldehyde fixative solutions can be used in the process of the present invention. Exemplary formaldehyde fixative solutions include NBF, paraformaldehyde, and others mentioned hereinabove.

In a preferred embodiment of the process, the quenching composition is placed in a volume of fixative at the same time as the biological specimen. After a delay, the quenching composition dissolves and disperses the formaldehyde-reactive agent. The agent then covalently reacts with and inactivates most of the formaldehyde.

In another method aspect, the present invention is directed to a method for fixing a biological sample. The method comprises contacting the sample with a fixative comprising formaldehyde to fix the tissue. The method further comprises contacting the fixative with at least one of the formaldehyde quenching compositions described above to quench the formaldehyde immediately or after a set period of time.

The biological sample may be single cells, tissues, organisms, viruses, and extracellular compositions.

Preferably, the sample volume is less than about 20% volume of the fixative.

A variety of analytical tests can be performed with better sensitivity and quality control when practiced either directly upon biological samples prepared using the present invention, or upon extracts prepared therefrom. These tests comprise the categories of immunoassays (e.g., IHC, flow immonocytochemistry, ELISA, immunoprecipitation, immunoblotting), assays for nucleic acid quantitation and sequence without amplification (e.g. in situ hybridization, quantitation) or with amplification methods (e.g., PCR in situ/in situ PCR, solution PCR, ligase chain reaction, strand displacement amplification), chromatographic methods (e.g., gas or liquid phase analyte transport), electrophoretic methods (capillary, slab gel) photometric methods (e.g., UV or visible or infra-red spectrophotometry, fluorimetry) and other methods for analysis of molecular compositions (e.g., mass spectroscopy, NMR).

In yet another method aspect, the present invention relates to a method of regulating the exposure of a biological sample to a fixative reagent. The method includes exposing a biological sample to a fixative reagent for a predetermined amount of time. The method further includes contacting the fixative reagent and the biological sample with an amount of fixative quenching reagent sufficient to substantially stop the fixation of the biological sample.

Preferably, the amount of time in which the biological sample is exposed to the fixative reagent is such that the biological sample is sufficiently stabilized from deterioration and putrefaction, but does not have the characteristics of prolonged exposure to the fixative reagent.

Even more preferably, the amount of time in which the biological sample is exposed to the fixative reagent is such that the biological sample is sufficiently stabilized from deterioration and putrefaction, but can be biochemically tested without substantial hinderance.

Having subjected the fixation time to strict quality control, the fixed and stabilized biological sample may be batched together with other similarly fixed samples for subsequent processing to achieve further economies of scale.

The present invention further relates to a biological sample treated according to the above-described processes.

EXAMPLES

The following examples are presented in further illustration of the present invention and should not be construed as unduly limiting of the scope thereof.

Example 1

Direct Compression Formulation of Core 1

A core is made comprising a lubricant, a disintegrant, succinic acid, and urea. The specific ingredients and their weight percentages are listed in Table 1 below.

TABLE 1

| | |
|---|---|
| 1. Urea | 76 wt % |
| 2. Avicel[1] | 10 wt % |
| 3. Succinic acid | 10 wt % |
| 4. AcDiSol[2] | 3.5 wt % |
| 5. Stearic acid | 0.5 wt % |

[1]Avicel is a trade name for Microcrystalline cellulose, N.F.
[2]AcDiSol is a trade name for Croscarmellose, N.F.

Ingredients 1 through 3 are first blended in a suitable blender for a sufficient time to ensure complete mixing. Ingredient 5 is then added to the mixture and blended for 5 min. Tablets are formed by compression using a standard tablet press and tablet press tooling.

Example 2

Direct Compression Formulation of Core 2

A core is made comprising a lubricant, a disintegrant, and urea. The specific ingredients and their weight percentages are listed in Table 2 below.

TABLE 2

| | |
|---|---|
| 1. Urea | 86 wt % |
| 2. Avicel[1] | 10 wt % |
| 3. Ac-Di-Sol[2] | 3.5 wt % |
| 4. Stearic acid | 0.5 wt % |

[1]Avicel is a trade name for Microcrystalline cellulose, N.F.
[2]Ac-Di-Sol is a trade name for Croscarmellose, N.F.

Ingredients 1 through 3 are first blended in a suitable blender for a sufficient time to ensure complete mixing. Ingredient 4 is then added and blended for 5 min. Tablets are compressed using a standard tablet press and tablet press tooling.

Example 3

Coating with Polymethacrylate Polymer

A polymethacrylate polymer is used to coat the tablets described in Example 1. This polymer interacts with a weak acid like succinic acid to give a delayed release profile. The formulation coated onto the tablets comprises a polymethacrylate polymer, talc, TEC, and water. The specific ingredients and their weight percentages are listed in Table 3 below.

TABLE 3

| | |
|---|---|
| 1. Eudragit RS 30D[1] | 40 wt % |
| 2. Talc | 6 wt % |
| 3. TEC[2] | 1 wt % |
| 4. Water | 53 wt % |

[1]Eudragit RS 30D is a trade name for polymethacrylate polymer containing ammonia methacrylate copolymer.
[2]TEC is an abbreviation for triethylcitrate.

Ingredients 1 through 4 are mixed to form an aqueous suspension and then sprayed onto the tablets using either standard pan coating or fluid bed technology.

Example 4

Coating with a Weak Acid and Polymethacrylate Polymer

The tablets described in Example 2 are first spray coated with a layer of a weak organic acid dissolved in a binder solution as formulated in Table 4 below. Then, a second layer consisting of a polymethacrylate polymer formulation as described in Table 3 above is sprayed on top of the organic acid layer. This polymer interacts with the weak acid to give a delayed release profile.

TABLE 4

| 1. Succinic acid | 33 wt % |
|---|---|
| 2. Sucrose | 33 wt % |
| 3. Water | 33 wt % |

Ingredients 1 and 2 are dissolved in water and then sprayed onto the tablets described in Example 2 using either standard pan coating or fluid bed technology.

Example 5

Coating with Poly(ortho ester) Polymer

In this example, a poly(ortho ester) polymer is used as a controlled release matrix for the quenching agent. The drug is released via the erosion of the polymer matrix. The erosion is caused by hydrolysis of the polymer by water.

Ingredients 1 and 2 listed in Table 5 below are mixed together and then filled into a hard gelatin capsule.

TABLE 5

| 1. Urea | 50 wt % |
|---|---|
| 2. Poly(ortho ester)[1] | 50 wt % |

[1]ca 5000 MW

Example 6

Effervescent Formulation

An effervescent tablet formulation is given in Table 6 below. The base tablet formulation is comprised of Na bicarbonate, citric acid, and urea.

TABLE 6

| 1. Citric acid, anhydrous (granular) | 40 wt % |
|---|---|
| 2. Na bicarbonate (granular) | 40 wt % |
| 3. Urea | 19 wt % |
| 4. Water | 1 wt % |

Ingredients 1 through 3 are thoroughly blended and water is rapidly added while mixing. Mixing is continued until a workable wet mass is formed. The mass is screened through a 10 mesh screen. The material is tray dried in a convection oven at 70° C. for 2 hours, then cooled and removed from the oven. It is then screened through a 16 mesh screen. The material is then mixed with a sufficient amount of a lubricant and compressed into tablets using a standard tablet press and tablet press tooling.

The resulting tablets are then spray coated using the coating solution and procedures described in Example 3.

Example 7

Efficacy of Active Ingredient

Pieces of rat ileum were placed in neutral buffered formaldehyde (NBF) immediately after excision. In FIGS. 1A and 1B, the tissue was fixed for 18 hours and then placed in ethanol for 29 days. In FIG. 1C, the tissue was kept in NBF for 30 days. In FIG. 1D, the tissue was fixed for 18 hours. An equimolar amount of urea was then added to the NBF. The tissue remained in this mixture for another 29 days. All tissues were then embedded in paraffin and sectioned to 5 $\mu$m thickness.

Immunohistochemical staining for the tissue antigen vimentin was then performed on the specimens using a standard monoclonal antibody V9 (FIGS. 1A, 1C, and 1D) or an isotype-matched control monoclonal (FIG. 1B). This was followed by detection using a secondary reagent, rabbit anti-mouse antibody conjugated with horseradish peroxidase polymer. Color was developed with diaminobenzidine and hydrogen peroxide as the peroxidase substrate (DAKO Envision System).

Immunohistochemical staining for vimentin revealed that staining intensity was very much fainter for specimens immersed in formaldehyde for 30 days. Specimens kept in formaldehyde and urea did not lose immunoreactivity and resembled those fixed for only a short time.

The results of this experiment clearly show the efficacy of quenching formaldehyde with urea in immunohistochemistry. The optimum molar ratio of urea to formaldehyde is not necessarily 1:1. However, this experiment documents real efficacy when such a ratio is used as described.

Example 8

Chemical Reaction of Urea and Formaldehyde

Urea (granular) was reacted with standard NBF to determine the rate and equilibrium extent of the chemical reaction. Formaldehyde calibrators and reaction residuals shown in FIGS. 2A and 2B, respectively, were measured using the spectrophotometric method of T. Nash (55 *Biochem. J.* 416–421 (1953)). This method involves measuring the light absorbance of the compound formed with acetylacetone at 405 nm. The assay for residual formaldehyde was validated for linearity by measuring serial dilutions of NBF as shown in FIG. 2A.

Figure 2B:
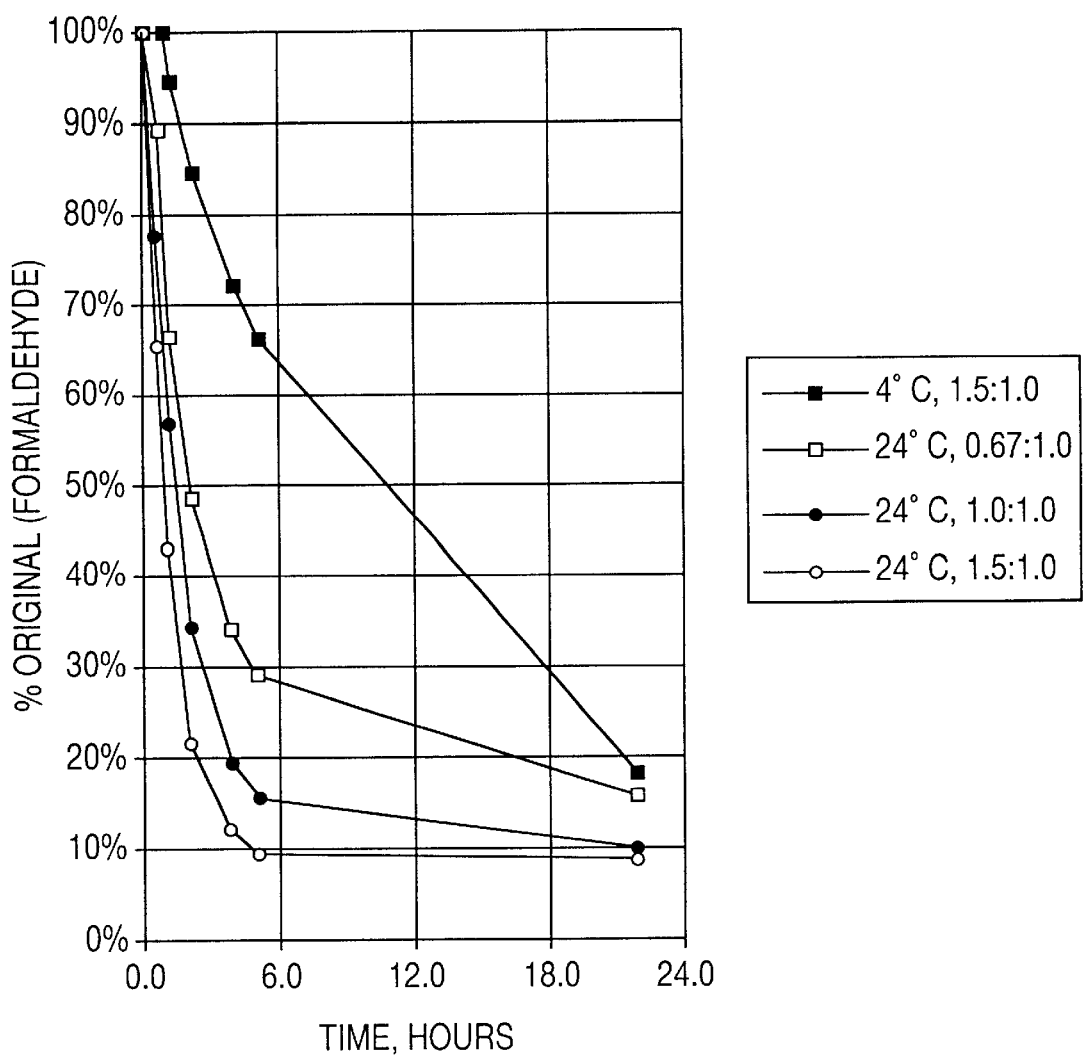
FIG. 2B shows the percent of original formaldehyde concentrations in NBF during four 21-hour reactions with urea.

Urea and formaldehyde in NBF were reacted at three different molar ratios and two temperatures. In FIG. 2B, the data show the residual formaldehyde concentrations that were measured in the reactions at the indicated times. Data were divided by the starting concentration and multiplied by 100 percent to express the percent of original concentration remaining.

The data of reaction at 24° C. of FIG. 2B show that the kinetic rate of reaction is relatively fast at urea: formaldehyde molar ratios of 1:1 and 1.5:1. At equilibrium, over 90% of the original concentration is quenched. This equates to a residual concentration of formaldehyde of about 0.12 M (0.33% w/v), and residual concentrations of urea of approximately 0.13 M at 1:1 or 0.2 M at 1.5:1. Equilibrium concentrations were stable for at least 39 days. These data also show that the rate of quenching is about ten times slower at 4° C. than at 24° C.

Example 9

Direct Compression Formulation of Core 3

A core is made of a lubricant, a disintegrant, succinic acid, ammonium bicarbonate and ammonium hydrogen phosphate. The specific ingredients and their weight percentages are listed in Table 7 below.

TABLE 7

| | |
|---|---|
| 1. Ammonium bicarbonate | 44 wt % |
| 2. Ammonium hydrogen phosphate | 32 wt % |
| 3. Avicel[1] | 10 wt % |
| 4. Succinic acid | 10 wt % |
| 5. AcDiSol[2] | 3.5 wt % |
| 6. Stearic acid | 0.5 wt % |

[1]Avicel is a trade name for Microcrystalline cellulose, N.F.
[2]AcDiSol is a trade name for Croscarmellose, N.F.

Ingredients 1 through 4 are first blended in a suitable blender for a sufficient time to ensure complete mixing. Ingredients 5 and 6 are then added to the mixture and blended for 5 min. Tablets are formed by compression using a standard tablet press and tablet press tooling.

Example 10

Direct Compression Formulation of Core 4

A core is made of a lubricant, a disintegrant, ammonium bicarbonate and ammonium hydrogen phosphate. The specific ingredients and their weight percentages are listed in Table 8 below.

TABLE 8

| | |
|---|---|
| 1. Ammonium bicarbonate | 32 wt % |
| 2. Ammonium hydrogen phosphate | 18 wt % |
| 3. Mannitol | 45 wt % |
| 4. Powdered PEG 8000 | 5% |

Ingredients 1 through 3 are first blended in a suitable blender for a sufficient time to ensure complete mixing. Ingredient 4 is then added to the mixture and blended for 5 min. Tablets are formed by compression using a standard tablet press and tablet press tooling.

Example 11

Wet Granulation Compression Formulation of Core 5

A core is made of a lubricant, filler/binder and active ingredients. The formulation is wet granulated before compression, the specific ingredients and their weight percentage are listed below in Table 9 below.

TABLE 9

| | |
|---|---|
| 1. Ammonium bicarbonate | 35% |
| 2. Ammonium hydrogen phosphate | 25% |
| 3. Microcrystalline cellulose | 39% |
| 4. Magnesium stearate | 1% |

Ingredients 1–3 are first blended in a suitable blender for a sufficient time to ensure complete mixing. Then a suitable granulation fluid is added to form a good granulation and then dried. Ingredient 4 is then added to the granulation and blended for 5 min. Tablets are formed by compression using a standard tablet press and tablet press tooling.

Example 12

Coating with a Weak Acid and Polymethacrylate Polymer

The tablets described in Example 10 are first spray coated with a layer of a weak organic acid dissolved in a binder solution as formulated in Table 10 below. Then, a second layer consisting of a polymethacrylate polymer formulation as described in Table 3 above is sprayed on top of the organic acid layer. This polymer interacts with the weak acid to give a delayed release profile.

TABLE 10

| | |
|---|---|
| 1. Succinic acid | 33 wt % |
| 2. Sucrose | 33 wt % |
| 3. Water | 33 wt % |

Ingredients 1 and 2 are dissolved in water and then sprayed onto the tablets described in Example 10 using either standard pan coating or fluid bed technology.

Example 13

Coating with Poly(ortho ester) Polymer

In this example, a poly(ortho ester) polymer is used as a controlled release matrix for the quenching agent. The drug is released via the erosion of the polymer matrix. The erosion is caused by hydrolysis of the polymer by water.

Ingredients 1–3 listed in Table 11 below are mixed together and then filled into a hard gelatin capsule.

TABLE 11

| | |
|---|---|
| 1. Ammonium bicarbonate | 29 wt % |
| 2. Ammonium hydrogen phosphate | 21 wt % |
| 3. Poly(ortho ester)[1] | 50 wt % |

[1]ca 5000 MW

Example 14

Sub-Coating with Hydroxypropyl Methylcellulose Polymer System

In this example, a hydroxypropyl methylcellulose polymer sub-coat is applied to any of the above examples before the main coat is applied. The sub-coating is a protective coating which is applied before the main coat. The sub-coat protects the moisture sensitive materials during the application of the main coat, thus allowing the coating of moisture sensitive materials. The sub-coating material can be applied using standard pan or fluid bed coating techniques. The specific ingredients and their weight percentages are listed in Table 12 below.

TABLE 12

| | |
|---|---|
| 1. Opadry solution[1] | 3 to 7.5 wt % |
| 2. Water | 97 to 92.5 wt % |

[1]containing 5% Opadry (commercially available from Colorcon, Pennsylvania).

The Opadry powder is dissolved in water (5%) and then slowly applied to the tablet using an atomizer at a temperature of 70° to 80° C. Typically, a coating level of 3 to 10 solids wt % of Opadry is applied to the tablet using standard pan or fluid bed coating techniques.

Example 15

Coating with Ethylcellulose Pseudo-Latex Polymer System

A ethylcellulose pseudo-latex polymer is used to coat the tablets which have been previously sub-coated as described in Example 14. The formulation coated onto the tablets comprises ethylcellulose pseudo-latex in water and a plasticizer. The specific ingredients and their suspension solids with percentages are listed in Table 13 below.

TABLE 13

| 1. Ethylcellulose pseudo-latex | 11 wt % |
| 2. Triethyl citrate | 4 wt % |
| 3. Water | 85 wt % |

Ingredients 1 through 3 are mixed to form an aqueous suspension and then sprayed onto the tablets using standard pan or fluid bed coating techniques.

Example 16

Efficacy of Active Ingredient

Quenching tablets used in this example were made of 0.5 gm ammonium bicarbonate, 0.19 gm of ammonium phosphate dibasic, and 0.34 gm of Avicell and magnesium stearate, and a coating of about 0.03 gm of Opadry (hydroxypropylmethylcellulose). One quenching tablet was added to 9.0 mL NBF, forming a mole ratio of 1:1 ammonium: formaldehyde.

Figure 3A:
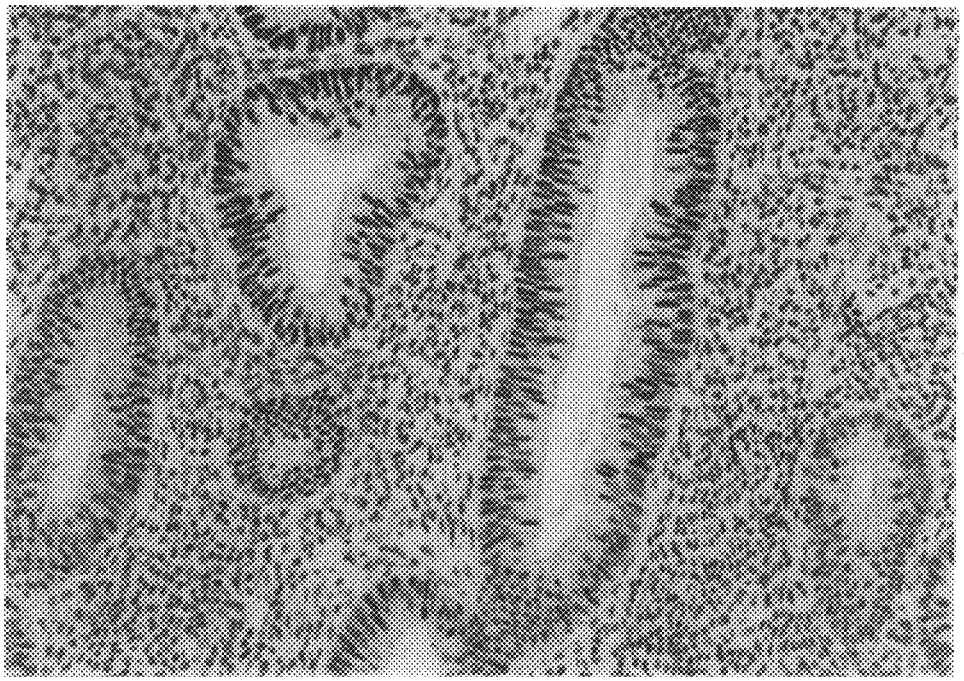
FIG. 3A shows a tissue sample that was fixed in NBF for 12 hours.
Figure 3B:
FIG. 3B shows a tissue sample that was fixed in NBF for 48 hours.
Figure 3C:
FIG. 3C shows another tissue sample that was fixed in NBF for 48 hours.
Figure 4A:
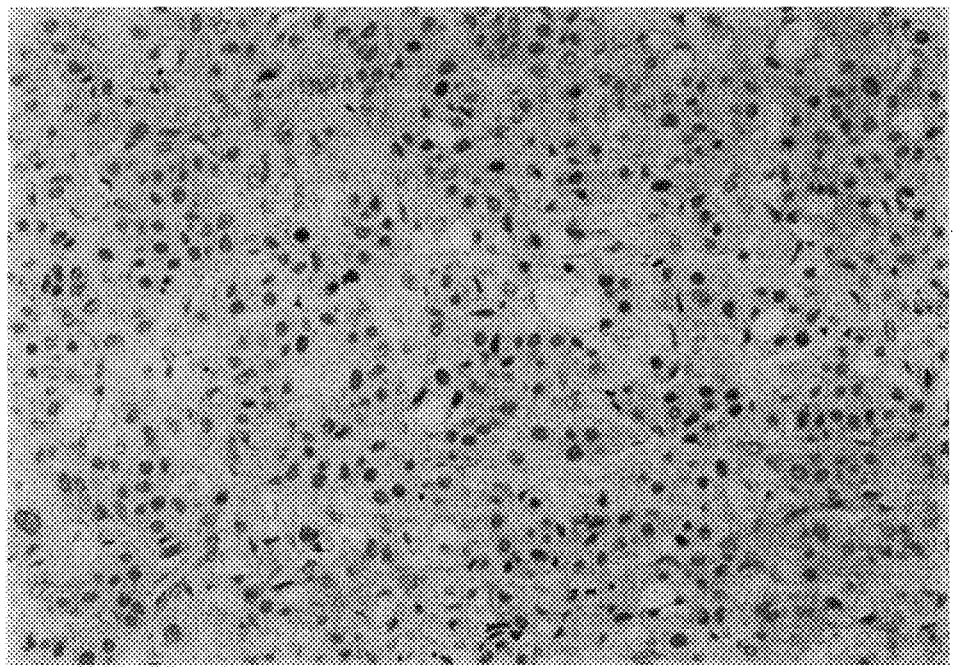
FIG. 4A shows a tissue sample that was fixed in NBF for 1 week.
Figure 4B:
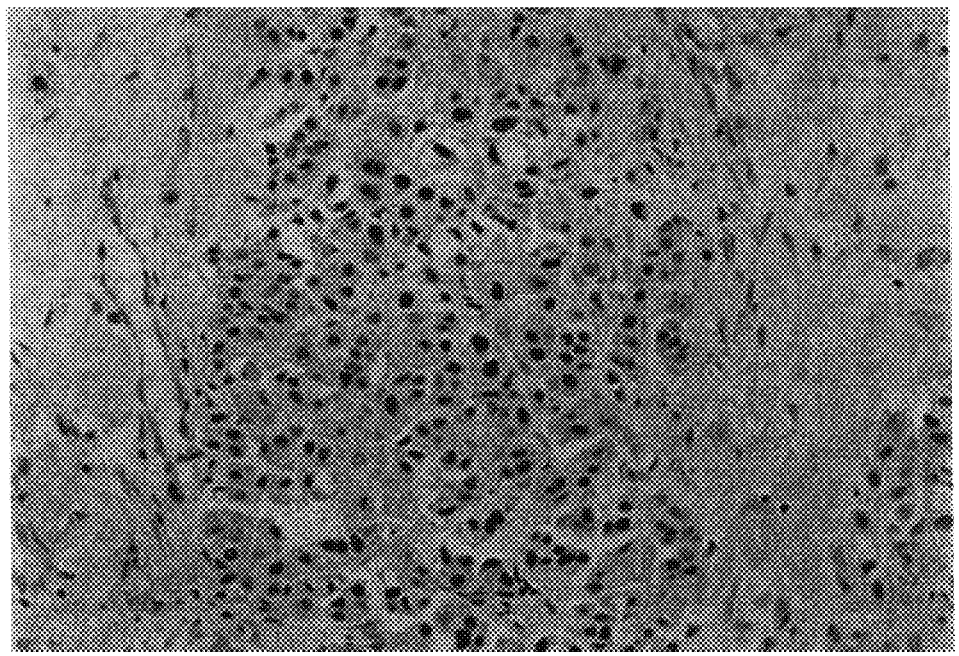
FIG. 4B shows another tissue sample that was fixed in NBF for 1 week.

Fresh surgical specimens of carcinoma and uterus tissue samples were collected and divided into pieces, which were placed in NBF immediately. In FIG. 3A, the tissue was fixed for 12 hours. In FIGS. 3B and 3C, the tissue was fixed for 48 hours. In FIGS. 4A and 4B, the tissued was fixed for 1 week. In FIGS. 3B and 4B, when the tissue had been fixed for one day, a quenching tablet was added, and the tissue remained in this mixture for another 36 hours or 6.5 days, respectively. All tissues were then dehydrated and embedded in paraffin and section to 5 µm thickness.

Immunohistochemical staining was performed using separate monoclonal antibodies to detect two nuclear antigens, which were the estrogen receptor (monoclonal antibody ER-IDS available from DAKO Corp., Carpinteria, Calif.) and the tumor supressor protein p53 (monoclonal antibody DO-7 available from DAKO Corp., Carpinteria, Calif.). This was followed by application of a secondary reagent, rabbit anti-mouse antibody conjugated with biotin (available from Sigma, St. Louis, Mo.). Detection reagent was then applied using a complex of avidin and biotinylated horseradish peroxidase (ABC reagent; Vector Laboratories). Color was developed using diaminobenzidine and hydrogen peroxide as the peroxidase substrate. Specimens kept in formaldehyde and ammonium salts did not lose much immunoreactivity and resembled those fixed for only a short time.

In FIG. 3A, immunohistochemical staining for estrogen receptor after only 12 hours of fixation revealed the basic intensity of staining with minimal fixation. In FIG. 4B, when the formaldehyde quenching tablet core was added after 24 hours, and specimen remained in fixative for a total of 48 hours, staining intensity and the fraction of all cells stained was similar. In FIG. 4C, the staining was less intense, and cell counts were significantly lower, for specimens immersed in formaldehyde for 48 hours without adding the formaldehyde quenching tablet.

In FIG. 4A, immunohistochemical staining for p53 revealed the intensity of staining when the formaldehyde quenching tablet core was added after 24 hours, and specimen remained in fixative for one week. In FIG. 4B, the staining was less intense, and cell counts were significantly lower for specimens immersed in formaldehyde for one week without adding the formaldehyde quenching tablet.

The results of this experiment clearly show the efficacy of quenching formaldehyde with ammonium salts in immunohistochemistry.

Example 17

Chemical Reaction of Buffered Ammonium Salts and Formaldehyde

Ammonium acetate ($NH_4C2.3H_2O$) was reacted with standard NBF to determine the rate and equilibrium extent of the chemical reaction. Formaldehyde calibrators and reaction residuals shown in FIGS. 2A and 5, respectively, were measured using the spectrophotometric method of T. Nash (55 Biochem. J. 416–421 (1953)). This method involves measuring light absorbency of the compound formed with acetylacetone at 405 nm. The assay for residual formaldehyde was validated for linearity by measuring serial dilutions of NBF ($\leq 0.0004X$) as shown in FIG. 2A.

Figure 5:
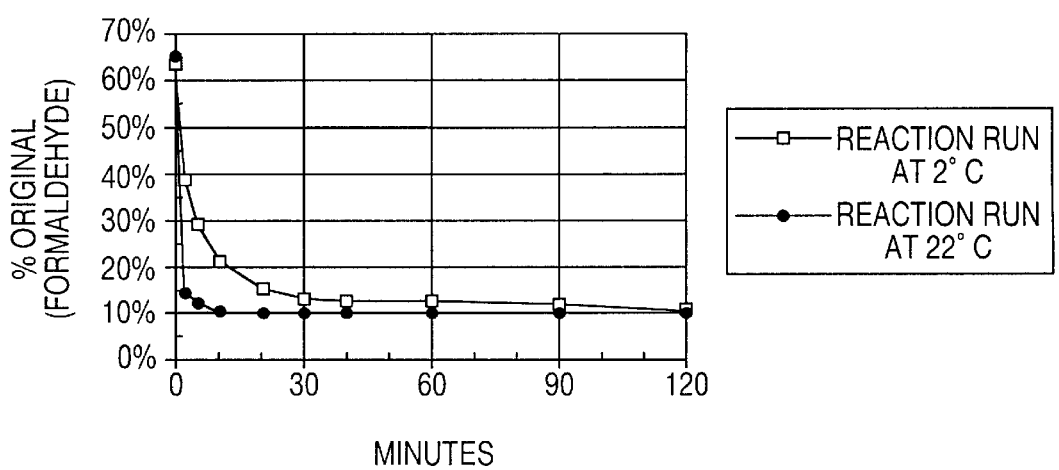
FIG. 5 shows the percent of original formaldehyde concentration over time in reactions with ammonium acetate.

Ammonium acetate and formaldehyde in NBF, also buffered with ancillary sodium carbonate were reacted at two temperatures at a ammonium:formaldehyde molar ratio of 1.5:1. In FIG. 5, the data show the residual formaldehyde concentration that were measured in the reactions at the indicated times. Data were divided by the starting concentration and multiplied by 100 percent to express the percent of original concentration remaining. The data of FIG. 5 show the kinetic rate of reaction has a very fast half time of about one minute at 22 ° C., and approaches equilibrium within 30 minutes. The data obtained at 4° C. (on ice) indicate a half time of about three minutes, which is still quite rapid. At both equilibria, at least 90% of the original formaldehyde concentration is quenched. A 10% residual concentration equates to about 0.12M (0.33% w/v). The capability of this assay method to accurately measure reaction of more than 90% of the formaldehyde in highly diluted samples of reaction products was not independently validated. Actual residual formaldehyde concentrations could be less than or equal to 10% of starting concentrations.

Example 18

Chemical Reactions of Eight Ammonium Salts and Formaldehyde

Eight different ammonium salts were reacted with neutral buffered formalin for one hour at a 1:1 mole ratio of ammonium to formaldehyde, and then the remaining formaldehyde concentrations were measured using the coloriometric assay of T. Nash (55 Biochem. J. 416–421 (1953)). The pH was measured at equilibrium using a calibrated pH meter after >12 hours. Data were divided by the starting concentration and multiplied by 100 percent to express the percent of original concentration remaining.

TABLE 14

| ammonium salt | ancillary NaHCO3 | final pH measured | % of initial [formaldehyde] left |
|---|---|---|---|
| chloride | none | 1.5 | 87% |
| thiocyanate | none | 1.7 | 84% |
| sulfate | none | 2.3 | 75% |
| phosphate, monobasic | none | 2.9 | 64% |
| phosphate, dibasic | none | 5.1 | 16% |
| acetate | none | 4.9 | 17% |
| acetate | 0.5 M | 5.6 | 17% |
| acetate bicarbonate: | 1.0 M | 7.0 | ≦12.4% |

TABLE 14-continued

| ammonium salt | ancillary NaHCO3 | final pH measured | % of initial [formaldehyde] left |
|---|---|---|---|
| phosphate, dibasic | | | |
| 40:60 (M:M)* | none | 6.0 | ≦11% |
| 50:50 (M:M)* | none | 6.3 | ≦10% |
| 60:40 (M:M)* | none | 6.7 | ≦10% |
| 70:30 (M:M)* | none | 7.0 | ≦10% |
| 80:20 (M:M)* | none | 7.3 | ≦10% |
| bicarbonate | none | 7.4 | ≦10% |
| tetraborate** | none | 9.3 | not done |

*molar ratio of anions
**ammonium tetraborate left an insoluble precipitate after the reaction The data of Table 14 indicate that, over the range of pH 1.5 to about pH 5.0, an inverse association exists between the extent of the reaction of quenching of formaldehyde and the pH. This is as would be predicted, because it is the ammonia ($NH_3$) species that actually reacts with formaldehyde, and mostly ammonium ion ($NH_4^+$) is present in acidic solutions. Addition of ancillary sodium bicarbonate buffer to neutralize the pH of the acetate reaction caused the formaldehyde concentration to decrease. The consumption of formaldehyde appeared to approach an asymptote between about pH 6.0 to pH 7.0. However, as stated above, actual residual formaldehyde concentrations could be less than or equal to 10% of starting concentrations.

The data of this Table further indicate that many ammonium salts, which are to considered as a class of compounds, are adequate to serve as the formaldehyde-reactive agent in the present invention, provided that an appropriate buffer is also present.

Ammonium bicarbonate has a particularly high capacity for quenching formaldehyde, because bicarbonate effectively neutralizes the pH of the reaction. Ammonium borate, though it is also a relatively alkaline buffer, left an insoluble residue in the fixative.

Other variations and modifications to the preferred embodiments described herein are intended to be encompassed by the true spirit and scope of the invention. This true spirit and scope are defined by the appended claims to be interpreted in light of the foregoing specification.

What is claimed is:

1. A composition comprising:
   (a) a first agent capable of chemically reacting with formaldehyde, and
   (b) a second agent capable of substantially preventing the first agent from chemically reacting with formaldehyde,
   wherein, if the composition is contacted with formaldehyde, then the second agent substantially prevents the first agent from chemically reacting with the formaldehyde for a finite period of time,
   wherein, after the finite period of time, the first agent chemically reacts with the formaldehyde,
   wherein, if 1.5 moles of the first agent and 1.0 moles of the formaldehyde are chemically reacted at 22° C., then the chemical reaction consumes at least about 90% of the formaldehyde within 20 minutes.

2. The composition of claim 1, wherein the first agent and the second agent do not substantially chemically react with biological tissue.

3. The composition of claim 1, wherein the first agent and the second agent do not substantially chemically react with protein or nucleic acid.

4. The composition of claim 1, wherein the first agent and the second agent are anhydrous.

5. The composition of claim 1, wherein the first agent is capable of chemically reacting with formaldehyde to form a compound which does not substantially chemically react with biological tissue.

6. The composition of claim 1, wherein the first agent is capable of dissolving in an aqueous solution to form an aqueous solution having a first-agent concentration of at least about 1.3 M.

7. The composition of claim 1, wherein the first agent is capable of dissolving in an aqueous solution at or below room temperature to form an aqueous solution having a first-agent concentration of at least about 0.25 M.

8. The composition of claim 1, wherein the first agent is urea.

9. The composition of claim 1, wherein the first agent is an ammonium salt.

10. The composition of claim 9, wherein the ammonium salt is selected from the group consisting of ammonium bicarbonate, ammonium phosphate dibasic, ammonium benzoate, ammonium alginate, ammonium bitartrate, ammonium citrate dibasic, ammonium chloride, ammonium gluconate, ammonium velerate, ammonium thiocyanate, ammonium phosphate monobasic, ammonium acetate, ammonium nitrate, ammonium sulfate, ammonium sulfamate, ammonium purpurate, ammonium tartrate, ammonium hippurate, ammonium iodide, ammonium bromide, ammonium fluoride, ammonium carbonate, and ammonium citrate.

11. The composition of claim 10, wherein the ammonium salt is ammonium bicarbonate.

12. The composition of claim 10, wherein the ammonium salt is a mixture of ammonium bicarbonate and ammonium phosphate dibasic.

13. The composition of claim 12, wherein the molar ratio of anions from ammonium bicarbonate to anions from ammonium phosphate dibasic is from about 50:50 to about 90:10.

14. The composition of claim 1, wherein the first agent is selected from the group consisting of an amino acid, a protein, a carbamic ester, a sugar in an alkaline solution, a malonic ester, a solid hydrazine, a dihydrochloride, a hemisulfate, a sulfate, a hydroxylamine, urea hydrogen peroxide, thiourea, cyanamide, dicyanamide, melamine, sodium bisulfate, hydrogen sulfide, aniline, and phenylhydrazine.

15. The composition of claim 1, wherein the second agent is a polymer.

16. The composition of claim 15, wherein the polymer is selected from the group consisting of polymethacrylate, ethylcellulose, poly(ortho ester), and polyvinyl pyrrolidone.

17. The composition of claim 1 comprising a dispersing agent.

18. The composition of claim 1, wherein the dispersing agent is an effervescent agent.

19. The composition of claim 18, wherein the effervescent agent is an intrinsic anion of an ammonium salt.

20. The composition of claim 18, wherein the effervescent agent is ammonium bicarbonate.

21. The composition of claim 1, wherein the effervescent agent is an organic and a carbonate.

22. The composition of claim 21, wherein the organic acid is selected from the group consisting of citric acid, tartaric acid, malic acid, fumaric acid, adipic acid, and succinic acid.

23. The composition of claim 21, wherein the carbonate is selected from the group consisting of sodium carbonate, sodium bicarbonate, potassium carbonate, potassium bicarbonate, sodium sesquicarbonate, sodium glycine carbonate, L-lysine carbonate, arginine carbonate, and calcium carbonate.

24. The composition of claim 1 comprising a pH neutralizer.

25. The composition of claim 24, wherein the pH neutralizer is a buffering agent or a base.

26. The composition of claim 24, wherein the pH neutralizer is an ammonium salt.

27. The composition of claim 1 comprising a buffering agent.

28. The composition of claim 27, wherein the buffering agent is an intrinsic anion of an ammonium salt.

29. The composition of claim 27, wherein the buffering agent is selected from the group consisting of ammonium bicarbonate, ammonium phosphate dibasic, and diammonium phosphate.

30. The composition of claim 29, wherein the buffering agent is a mixture of ammonium bicarbonate and ammonium phosphate dibasic.

31. The composition of claim 1, wherein the composition is in the form of a tablet, pellet, or capsule.

32. The composition of claim 1 comprising a core and a coating layer surrounding the core, wherein the core contains the first agent and the coating layer contains the second agent.

33. The composition of claim 32, wherein the core comprises a lubricant.

34. The composition of claim 33, wherein the lubricant is selected from the group consisting of sodium lauryl sulfate, sodium benzoate, polyethylene glycol 8000, magnesium stearate, and sodium stearyl fumarate.

35. The composition of claim 32, wherein the core comprises a filler or binder.

36. The composition of claim 35, wherein the filler or binder is selected from the group consisting of microcrystalline cellulose, dextrose, lactose, and mannitol.

37. The composition of claim 32, wherein the coating layer comprises a polymer.

38. The composition of claim 37, wherein the polymer is selected from the group consisting of polymethacrylate, ethylcellulose, poly(ortho ester), and polyvinyl pyrrolidone.

39. The composition of claim 32, wherein the coating layer comprises a plasticizing agent.

40. The composition of claim 32 comprising a subcoating layer surrounding the core, wherein the subcoating layer is interposed between the core and the coating layer.

41. The composition of claim 40, wherein the subcoating layer comprises hydroxypropylmethylcellulose.

42. The composition of claim 40, wherein the subcoating layer comprises a plasticizing agent.

43. A composition comprising:
(a) a first agent capable of chemically reacting with formaldehyde, and
(b) a second agent capable of substantially preventing the first agent from chemically reacting with formaldehyde,
wherein, if the composition is contacted with formaldehyde, then the second agent substantially prevents the first agent from chemically reacting with the formaldehyde for a finite period of time,
wherein, after the finite period of time, the first agent chemically reacts with the formaldehyde,
wherein, if 1.5 moles of the first agent and 1.0 moles of the formaldehyde are chemically reacted at 2° C., then the chemical reaction consumes at least about 90% of the formaldehyde within 120 minutes.

44. The composition of claim 43, wherein the first agent and the second agent do not substantially chemically react with biological tissue.

45. The composition of claim 43, wherein the first agent and the second agent do not substantially chemically react with protein or nucleic acid.

46. The composition of claim 43, wherein the first agent and the second agent are anhydrous.

47. The composition of claim 43, wherein the first agent is capable of chemically reacting with formaldehyde to form a compound which does not substantially chemically react with biological tissue.

48. The composition of claim 43, wherein the first agent is capable of dissolving in an aqueous solution to form an aqueous solution having a first-agent concentration of at least about 1.3 M.

49. The composition of claim 43, wherein the first agent is capable of dissolving in an aqueous solution at or below room temperature to form an aqueous solution having a first-agent concentration of at least about 0.25 M.

50. The composition of claim 43, wherein the first agent is urea.

51. The composition of claim 43, wherein the first agent is an ammonium salt.

52. The composition of claim 51, wherein the ammonium salt is selected from the group consisting of ammonium bicarbonate, ammonium phosphate dibasic, ammonium benzoate, ammonium alginate, ammonium bitartrate, ammonium citrate dibasic, ammonium chloride, ammonium gluconate, ammonium velerate, ammonium thiocyanate, ammonium phosphate monobasic, ammonium acetate, ammonium nitrate, ammonium sulfate, ammonium sulfamate, ammonium purpurate, ammonium tartrate, ammonium hippurate, ammonium iodide, ammonium bromide, ammonium fluoride, ammonium carbonate, and ammonium citrate.

53. The composition of claim 52, wherein the ammonium salt is ammonium bicarbonate.

54. The composition of claim 52, wherein the ammonium salt is a mixture of ammonium bicarbonate and ammonium phosphate dibasic.

55. The composition of claim 54, wherein the molar ratio of anions from ammonium bicarbonate to anions from ammonium phosphate dibasic is from about 50:50 to about 90:10.

56. The composition of claim 43, wherein the first agent is selected from the group consisting of an amino acid, a protein, a carbamic ester, a sugar in an alkaline solution, a malonic ester, a solid hydrazine, a dihydrochloride, a hemisulfate, a sulfate, a hydroxylamine, urea hydrogen peroxide, thiourea, cyanamide, dicyanamide, melamine, sodium bisulfate, hydrogen sulfide, aniline, and phenylhydrazine.

57. The composition of claim 43, wherein the second agent is a polymer.

58. The composition of claim 57, wherein the polymer is selected from the group consisting of polymethacrylate, ethylcellulose, poly(ortho ester), and polyvinyl pyrrolidone.

59. The composition of claim 43 comprising a dispersing agent.

60. The composition of claim 43, wherein the dispersing agent is an effervescent agent.

61. The composition of claim 60, wherein the effervescent agent is an intrinsic anion of an ammonium salt.

62. The composition of claim 60, wherein the effervescent agent is ammonium bicarbonate.

63. The composition of claim 43, wherein the effervescent agent is an organic acid and a carbonate.

64. The composition of claim 63, wherein the organic acid is selected from the group consisting of citric acid, tartaric acid, malic acid, fumaric acid, adipic acid, and succinic acid.

65. The composition of claim 63, wherein the carbonate is selected from the group consisting of sodium carbonate, sodium bicarbonate, potassium carbonate, potassium bicarbonate, sodium sesquicarbonate, sodium glycine carbonate, L-lysine carbonate, arginine carbonate, and calcium carbonate.

66. The composition of claim 43 comprising a pH neutralizer.

67. The composition of claim 66, wherein the pH neutralizer is a buffering agent or a base.

68. The composition of claim 66, wherein the pH neutralizer is an ammonium salt.

69. The composition of claim 43 comprising a buffering agent.

70. The composition of claim 69, wherein the buffering agent is an intrinsic anion of an ammonium salt.

71. The composition of claim 69, wherein the buffering agent is selected from the group consisting of ammonium bicarbonate, ammonium phosphate dibasic, and diammonium phosphate.

72. The composition of claim 71, wherein the buffering agent is a mixture of ammonium bicarbonate and ammonium phosphate dibasic.

73. The composition of claim 43, wherein the composition is in the form of a tablet, pellet, or capsule.

74. The composition of claim 43 comprising a core and a coating layer surrounding the core, wherein the core contains the first agent and the coating layer contains the second agent.

75. The composition of claim 74, wherein the core comprises a lubricant.

76. The composition of claim 75, wherein the lubricant is selected from the group consisting of sodium lauryl sulfate, sodium benzoate, polyethylene glycol 8000, magnesium stearate, and sodium stearyl fumarate.

77. The composition of claim 74, wherein the core comprises a filler or binder.

78. The composition of claim 77, wherein the filler or binder is selected from the group consisting of microcrystalline cellulose, dextrose, lactose, and mannitol.

79. The composition of claim 74, wherein the coating layer comprises a polymer.

80. The composition of claim 79, wherein the polymer is selected from the group consisting of polymethacrylate, ethylcellulose, poly(ortho ester), and polyvinyl pyrrolidone.

81. The composition of claim 74, wherein the coating layer comprises a plasticizing agent.

82. The composition of claim 74 comprising a subcoating layer surrounding the core, wherein the subcoating layer is interposed between the core and the coating layer.

83. The composition of claim 82, wherein the subcoating layer comprises hydroxypropylmethylcellulose.

84. The composition of claim 82, wherein the subcoating layer comprises a plasticizing agent.

* * * * *